(12) United States Patent
Muratoglu

(10) Patent No.: US 7,205,339 B2
(45) Date of Patent: Apr. 17, 2007

(54) SELECTIVE CONTROLLED MANIPULATION OF POLYMERS

(75) Inventor: Orhun K. Muratoglu, Cambridge, MA (US)

(73) Assignee: Massachusetts General Hospital, Boston, MA (US)

( * ) Notice: Subject to any disclaimer, the term of this patent is extended or adjusted under 35 U.S.C. 154(b) by 24 days.

(21) Appl. No.: 10/433,987

(22) PCT Filed: Dec. 11, 2001

(86) PCT No.: PCT/US01/47507

§ 371 (c)(1),
(2), (4) Date: Sep. 24, 2003

(87) PCT Pub. No.: WO02/48259

PCT Pub. Date: Jun. 20, 2002

(65) Prior Publication Data

US 2004/0051213 A1  Mar. 18, 2004

Related U.S. Application Data

(60) Provisional application No. 60/254,560, filed on Dec. 12, 2000.

(51) Int. Cl.
  *C08L 23/00* (2006.01)
  *C08L 23/06* (2006.01)
  *A61F 2/30* (2006.01)
  *C08J 3/28* (2006.01)

(52) U.S. Cl. ............... 522/161; 522/150; 522/162; 526/352; 623/23.58

(58) Field of Classification Search ............... 522/161, 522/150, 162; 526/352; 623/23.58
See application file for complete search history.

(56) References Cited

U.S. PATENT DOCUMENTS

| 5,879,400 A | 3/1999 | Merrill et al. ............... 623/22 |
| 6,365,089 B1 | 4/2002 | Krebs et al. ............... 264/485 |
| 6,818,171 B2 | 11/2004 | Wang et al. ............... 264/478 |

FOREIGN PATENT DOCUMENTS

| WO | WO97/29793 | 8/1997 |
| WO | WO01/05337 | 7/1999 |
| WO | WO99/52474 | 10/1999 |

*Primary Examiner*—Susan Berman
(74) *Attorney, Agent, or Firm*—Proskauer Rose LLP

(57) ABSTRACT

The present invention provides partial and complete shielding approaches to alter the cross-linking characteristics of irradiated polymers, such as polyethylene. Irradiated polymers and fabricated articles, such as medical prosteses, comprising irradiated polymers also are provided.

22 Claims, 24 Drawing Sheets

FIG. 12
PERIPHERY SHIELD CROSS-SECTIONS
CORE SHIELD CROSS-SECTIONS
a   a 
b   b 
c   c 
d   d 
e   e 
f   f 
g   g 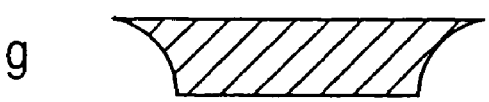

FIG. 15
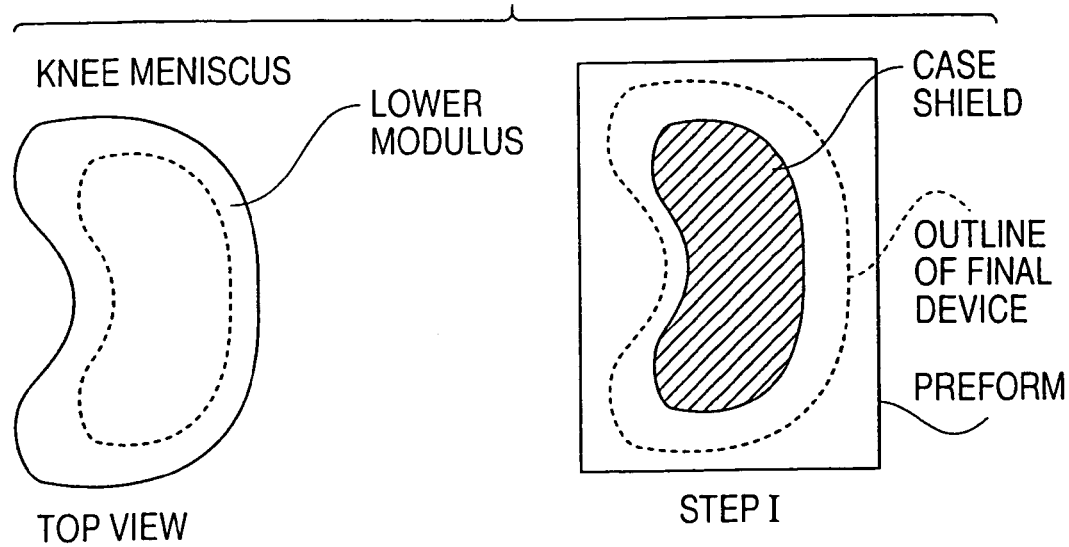
KNEE MENISCUS — LOWER MODULUS
TOP VIEW
STEP I — CASE SHIELD, OUTLINE OF FINAL DEVICE, PREFORM
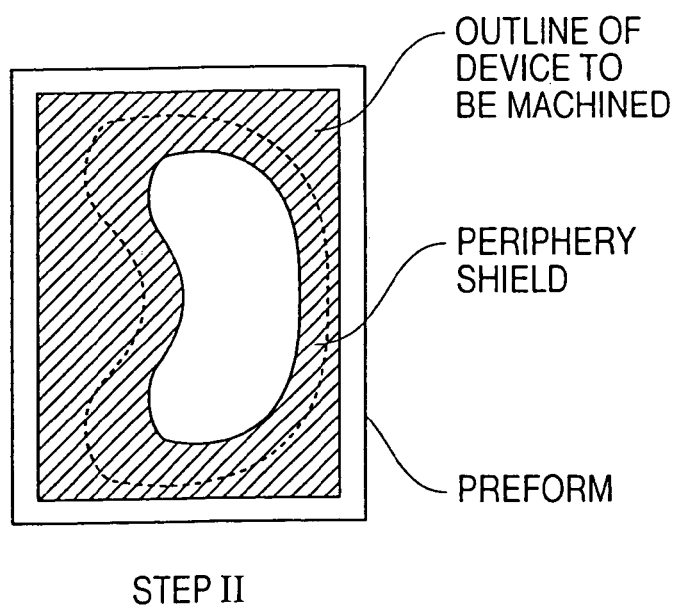
STEP II — OUTLINE OF DEVICE TO BE MACHINED, PERIPHERY SHIELD, PREFORM

FIG. 16
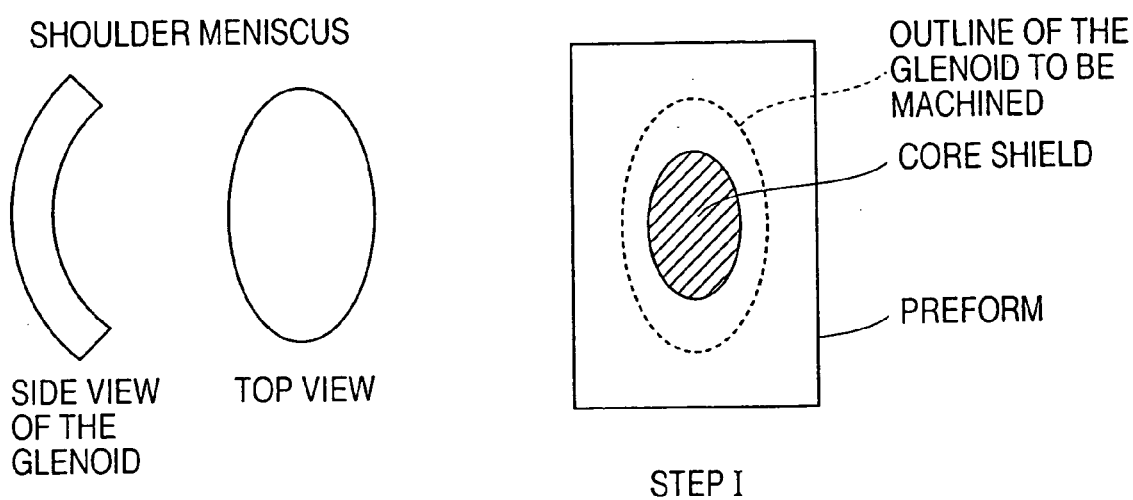
SHOULDER MENISCUS
SIDE VIEW OF THE GLENOID
TOP VIEW
OUTLINE OF THE GLENOID TO BE MACHINED
CORE SHIELD
PREFORM
STEP I
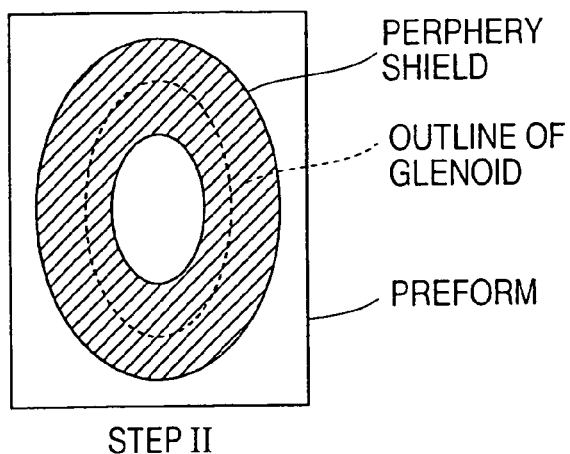
PERPHERY SHIELD
OUTLINE OF GLENOID
PREFORM
STEP II

SELECTIVE CONTROLLED MANIPULATION OF POLYMERS

RELATED APPLICATION

This application is a 371 of PCT/US01/47507 filed on Dec. 11, 2001, which claims benefit to U.S. Provisional No. 60/254,560, filed on Dec. 12, 2000, the entirety of which is hereby incorporated by reference.

BACKGROUND OF THE INVENTION

The present invention relates to the selective, controlled manipulation of polymers and polymer alloys using radiation chemistry, which makes possible the tailoring of polymer properties for a specific intended use. The present invention finds particular application in the orthopedic field, including the formation of medical prosthesis, such as hip, knee, shoulder, and finger implants.

Methods of irradiating polymers are described in U.S. Pat. No. 5,879,400. In general, this patent describes medical prosthesis formed, at least in part, of a melt-irradiated high molecular weight polyethylene. The disclosed melt-irradiation process improves the wear resistance of the polymer, thus addressing the problem of severe adverse effects associated with the use of less wear resistant polymers. U.S. Pat. No. 5,879,400 describes, among other things, heating the polymers to or above the melting point, irradiating the polymer, and cooling the polymer.

International Application No. PCT/US97/02220 (WO 97/29793) also describes the irradiation of polymers that are useful in the orthopedic field. In this application, several methods of increasing the wear characteristics of polymers are described. The application describes, among other things, an irradiation procedure wherein the polymer is irradiated at room temperature or below. Following irradiation, the polymer can be heated to or above the melting temperature to remove any residual free radicals through the process of recombination. The application also describes another irradiation method in which the polymer is preheated to a temperature above room temperature, but below the melting temperature, and irradiated. Following irradiation, the polymer may be subsequently melted by heating it to the melting temperature or above to substantially eliminate any detectable free radicals via the process of recombination.

WO 97/29793 also describes methods of irradiating polymers in which the heat generated by the irradiation is sufficient to at least partially melt the polymer, and is described as "adiabatic melting". "Adiabatic melting" refers to heating induced by radiation, which leads to an increase of the temperature of the polymer with substantially little loss of heat to the surroundings. The application describes an adiabatic melting method in which the polymer is preheated to a temperature below the melting point, then irradiated with enough total dose and at a high enough dose rate to at least partially melt the polymer crystals. Subsequent to this warm-irradiation, the polymer also can be heated to or above the melting temperature such that any residual free radicals are eliminated. The application also describes another irradiation, adiabatic melting method that is similar to the method described above, except that the polymer is provided at room temperature or below.

International Application No. PCT/US99/16070, describes the use of irradiated polymers for hip joints with an extended range of motion. In particular, this application relates to the use of wear resistant irradiated polymers in hip joint prostheses. The wear resistance of the polymers allows for the use of combinations of cup thicknesses and head diameters that result in an extended range of motion as compared with conventional replacement hip joints, the wear resistance of which was unable to support cup thickness and head diameter combinations that allowed for extended ranges of motion.

Other approaches of irradiation are disclosed in U.S. Pat. Nos. 6,281,264; 6,245,276; 6,242,507; 6,228,900; 6,184,265; 6,165,220; and 6,017,975.

Despite the major improvements in the wear resistance of orthopedic prostheses and the design of hip prostheses allowing an improved range of motion, there remains a significant need for further improvements. For example, the irradiation of polymers is known to change the mechanical properties of the polymer. Following irradiation and subsequent melting and annealing, polyethylene polymers exhibit reduced toughness, reduced modulus of elasticity, reduced shear strength and reduced ultimate tensile strength. In the case of hip prostheses, for example, larger head diameters often require the use of thinner liners. The locking mechanisms on these liners (used to lock the liner to metal shells) may fail due to the undesirable changes in the mechanical properties of the polymers following irradiation. The situation is similar in knee prostheses. In knee prostheses, intricate locking mechanism, usually in the form of snap-lock, pegs and pins, are used to stabilize the liners on a metal tray. These locking mechanisms rely on the high shear strength of the polymer used. When irradiated, the adverse effects on the shear strength of the polymer may jeopardize the stability of the liner. Similar problems arise in other types of medical prostheses.

These and other aspects of the invention will become apparent to the skilled artisan in view of the teachings contained herein.

SUMMARY OF THE INVENTION

It is an object of the present invention to provide improved polymers for various uses, including medical uses such as prosthetics. In accomplishing this object and other objects, there are provided, in accordance with one aspect of the invention, an irradiated composition comprising a polymer, wherein the composition having a gradient of cross-linking perpendicular to the direction of irradiation. The polymer can be selected from the group consisting of high density polyethylene, low density polyethylene, linear low density polyethylene, ultra low density polyethylene, very low density polyethylene, ultra high molecular weight polyethylene, and high molecular weight polyethylenes.

In accordance with another aspect of the invention, there are provided methods of making a cross-linked composition comprising an irradiated polymer, said cross-linked composition having a gradient of cross-linking perpendicular to the direction of irradiation, wherein the method comprises:

(A) shielding part or all of composition comprising a polymer; and (B) irradiating said partially shielded composition of (A) to yield the cross-linked polymer. The shield can be made of, among other things, a material selected from the group consisting of ceramics, metals, glass and polymers. The polymer can be selected from the group consisting of high density polyethylene, low density polyethylene, linear low density polyethylene, ultra low density polyethylene, very low density polyethylene, ultra high molecular weight polyethylene, and high molecular weight polyethylene. According to one aspect of the invention, the irradiation step comprises one or more, in any order, of the procedures selected from the group consisting of procedures (a)–(g):

(a) (i) heating the polymer to at or above the melting temperature of the polymer, and
(ii) irradiating the polymer in the molten state;
(b) (i) providing the polymer at or below room temperature, and
(ii) irradiating the polymer;
(c) (i) providing the polymer at or below room temperature, and
(ii) irradiating the polymer with a high enough total dose and/or at a fast enough dose rate to generate enough heat in the polymer to result in at least a partial melting of the crystals of the polymer;
(d) (i) providing the polymer at or below room temperature,
(ii) irradiating the polymer, and
(iii) heating the irradiated polymer to at or above the melting temperature of the polymer;
(e) (i) heating the polymer to a temperature above room temperature and below the melting temperature, and
(ii) irradiating the heated polymer;
(f) (i) heating the polymer to a temperature above room temperature and below the melting temperature,
(ii) irradiating the heated polymer, and
(iii) heating the irradiated polymer to at or above the melting temperature of the polymer; and/or
(g) (i) heating the polymer to a temperature above room temperature and below the melting temperature, and
(ii) irradiating the heated polymer with a high enough total dose and/or at a fast enough dose rate to generate enough heat in the polymer to result in at least a partial melting of the crystals of the polymer.

In accordance with another aspect of the invention, there are provided medical prostheses comprising an irradiated polymer, said prosthesis having a gradient of cross-linking perpendicular to the direction of irradiation. The polymer can be selected from the group consisting of high density polyethylene, low density polyethylene, linear low density polyethylene, ultra low density polyethylene, very low density polyethylene, ultra high molecular weight polyethylene, and high molecular weight polyethylene.

In accordance with still another aspect of the invention, there are provided methods of making medical prostheses comprising an irradiated polymer, said medical prosthesis having a gradient of cross-linking perpendicular to the direction of irradiation, said method comprising:

(A) shielding part or all of a composition comprising said polymer; and
(B) irradiating said partially shielded composition. The shield can be made of, among other things, a material selected from the group consisting of ceramics, metals, glasses and polymers. The polymer can be selected from the group consisting of high density polyethylene, low density polyethylene, linear low density polyethylene, ultra low density polyethylene, very low density polyethylene, ultra high molecular weight polyethylene, and high molecular weight polyethylene. According to one aspect of the invention, the irradiation step comprises one or more, in any order, of the procedures selected from the group consisting of procedures (a)–(g):

(a) (i) heating the polymer to at or above the melting temperature of the polymer, and
(ii) irradiating the polymer in the molten state;
(b) (i) providing the polymer at or below room temperature, and
(ii) irradiating the polymer;
(c) (i) providing the polymer at or below room temperature, and
(ii) irradiating the polymer with a high enough total dose and/or at a fast enough dose rate to generate enough heat in the polymer to result in at least a partial melting of the crystals of the polymer;
(d) (i) providing the polymer at or below room temperature,
(ii) irradiating the polymer, and
(iii) heating the irradiated polymer to at or above the melting temperature of the polymer;
(e) (i) heating the polymer to a temperature above room temperature and below the melting temperature, and
(ii) irradiating the heated polymer;
(f) (i) heating the polymer to a temperature above room temperature and below the melting temperature,
(ii) irradiating the heated polymer, and
(iii) heating the irradiated polymer to at or above the melting temperature of the polymer; and/or
(g) (i) heating the polymer to a temperature above room temperature and below the melting temperature, and
(ii) irradiating the heated polymer with a high enough total dose and/or at a fast enough dose rate to generate enough heat in the polymer to result in at least a partial melting of the crystals of the polymer.

The invention is further disclosed and exemplified by reference to the text and drawings that follow.

BRIEF DESCRIPTION OF THE DRAWINGS

FIG. 2 shows that the crosslink distribution in the CISM process is more statistical (random) in the amorphous phase as compared with the WIAM process, in which the final crosslink distribution is highly non-uniform with a biphasic structure. X represents the crystallinity and T represents temperature. Here, the "% dose" indicates the percent of the total radiation dose intended to be delivered to the polymer during the irradiation step.

FIG. 12 depicts various exemplary shield geometry's, which can be used according to the invention, such as in an arrangement according to FIG. 21.

FIG. 15 depicts the use of the present invention in the fabrication of a knee meniscus prosthesis.

FIG. 16 depicts the use of the present invention in the fabrication of a shoulder meniscus prosthesis.

DETAILED DESCRIPTION OF THE INVENTION

Figure 1:
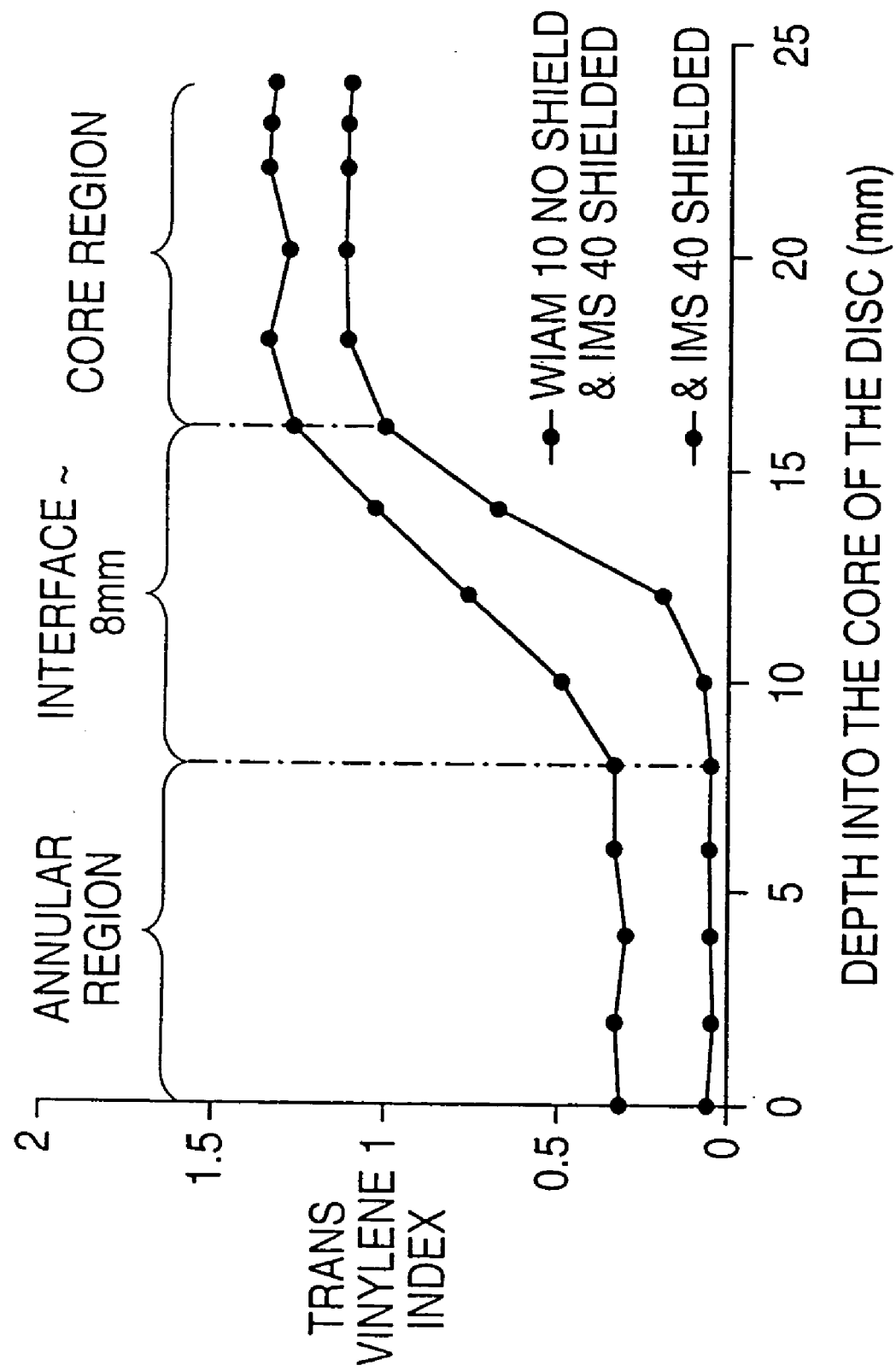
FIG. 1 is a graph plotting the trans vinylene index versus the depth into the core of an irradiated ultra-high molecular weight polyethylene ("UHMWPE") disc.

The present invention relates to the selective, controlled irradiation manipulation of polymers, including (1) compositions that are homogenous in terms of a given type of polymer content (for example, homopolymers), and (2) polymer alloys. The manipulation of the polymers, as described herein, allows the tailoring of the physical properties of the polymers to achieve a desired result. The polymers may be used in a variety of applications, including in the manufacture of medical prostheses.

By "ultra-high molecular weight polyethylene" or "UHMWPE" is meant chains of ethylene that have molecular weights in excess of about 500,000 g/mol, preferably above about 1,000,000 g/mol, and more preferably above about 2,000,000 g/mol. Often the molecular weights can be at least as high as about 8,000,000 g/mol. By initial average molecular weight is meant the average molecular weight of the UHMWPE starting material, prior to any irradiation.

By "low-density polyethylene" or LDPE is meant a polyethylene with a density range of about 0.910–0.932 g/cm$^3$. The LDPE is usually polymerized from ethylene gas in presence of a few mol percent of a co-monomer (1-pentene, 1-hexene, etc.) with shorter branches.

By "high-density polyethylene" or HDPE is meant a polyethylene with a density in excess of about 0.936 g/cm$^3$. The HDPE is usually polymerized from ethylene gas in presence of a few mol percent of a co-monomer (1-pentene, 1-hexene, etc.) to achieve substantially unbranched polyethylene chains.

By "linear-low-density polyethylene" or LLDPE is meant a polyethylene with a density range of about 0.910–0.942 g/cm$^3$. The LLDPE is polymerized from ethylene gas with the addition of short branches (shorter than LDPE) to keep the density lower than what is observed in HDPE. LLDPEs are copolymers of ethylene and alpha-olefins polymerized with either Ziegler-Natta or metallocene catalysts. The molecular structure exhibits short-chain branching. Generally, the metallocene chemistry yields a more uniform distribution of the short-chain branches than Ziegler-Natta catalysts.

The term "embodiment" is non-limiting and includes examples and aspects of the invention, which are combinable in view of the teachings contained herein.

The term "about" in the context of numerical values and ranges refers to values or ranges that approximate or are close to the recited values or ranges such that the invention can perform as intended, such as having a desired degree of cross-linking and/or a desired lack of free radicals, as is apparent from the teachings contained herein. This term encompasses values beyond those resulting from systematic error.

Examples of commercially-available UHMWPE resins (in powder form) include Hifax Grade 1900 polyethylene (obtained from Montell, Wilmington, Del.), having a molecular weight of about 2 million g/mol and not containing any calcium stearate; GUR 1050 (obtained from Hoechst Celanese Corp., Germany), having a molecular weight of about 4–5 million g/mol and not containing any calcium stearate; GUR 1150 (obtained from Hoechst Celanese Corp., Germany), having a molecular weight of about 4–5 million g/mol and containing 500 ppm of calcium stearate; GUR 1020 (obtained from Hoechst Celanese Corp., Germany), having a molecular weight of about 2 million g/mol and not containing any calcium stearate; and GUR 1120 (obtained from Hoechst Celanese Corp., Germany), having a molecular weight of about 2 million g/mol and containing 500 ppm of calcium stearate. Preferred UHMWPEs for medical applications are GUR 1050 and GUR 1020. By resin is meant powder.

UHMWPE powder can be consolidated using a variety of different techniques, e.g., ram extrusion, compression molding, or direct compression molding. In ram extrusion, the UHMWPE powder is pressurized through a heated barrel whereby it is consolidated into a rod stock, i.e., bar stock (can be obtained, e.g., from Westlake Plastics, Lenni, Pa.). In compression molding, the UHMWPE powder is consolidated under high pressure into a mold (can be obtained, e.g., from Poly-Hi Solidur, Fort Wayne, Ind., or Perplas, Stanmore, U.K.). The shape of the mold can be, e.g., a thick sheet. Direct compression molding is preferably used to manufacture net shaped products, e.g., acetabular components or tibial knee inserts (can be obtained, e.g., from Zimmer, Inc., Warsaw, Ind.). In this technique, the UHMWPE powder is compressed directly into the final shape.

Some of the commercial sources of LDPE along with approximate density ranges are as follows: Novapol (0.917–0.924 g/cm³) from Nova Chemical, Petrothene (0.9175–0.932 g/cm³) from Equistar, and Escorene (0.913–0.929 g/cm³) from Exxon Mobile. The LDPE generally exhibits density ranges of about 0.910 and 0.932 g/cm³.

Some of the commercial sources of HDPE along with approximate density ranges area as follows: Sclair (0.936–0.962 g/cm³) and Novapol (0.945–0.956 g/cm³) from Nova Chemical, Alathon (0.949–0.965 g/cm³) and Petrothene (0.940–0.961 g/cm³) from Equistar, and Escorene (0.941–0.966 g/cm³) from Exxon Mobile. The HDPE generally exhibits a density of larger than about 0.936 g/cm³.

Some of the commercial sources of LLDPE along with approximate density ranges are as follows: Dowlex (0.917–0.941 g/cm³) from Dow Chemical, Novapol (0.917–0.926 g/cm³) and Sclair (0.918–0.930 g/cm³) from Nova Chemical, Petrothene (0.918–0.9305 g/cm³) from Equistar, and Escorene (0.917–0.938 g/cm³) from Exxon Mobile. The LLDPE generally exhibits density ranges of about 0.910 and 0.942 g/cm³.

Some of the commercial sources of VLDPE or ULDPE along with approximate densities are as follows: Attane (ranging from about 0.904–0.913 g/cm³) from Dow Chemical, Sclair (0.911 g/cm³) from Nova Chemical. These VLDPE and ULDPE generally exhibit a density of less than about 0.913 g/cm³.

Use of the phrases such as "radiation treated," "irradiated," or the like, mean that the polymer or polymer alloy have been treated with radiation, including gamma radiation or electron radiation, so as to induce cross-links between the polymeric chains of the polymer.

"Substantially no detectable free radicals" means that substantially no free radicals are present to deleteriously affect the desired properties of the irradiated material and can be measured as described in Jahan et al., *J. Biomedical Materials Research* 25:1005 (1991). Free radicals include, for example, allyl and/or alkyl type or peroxy type free radicals. A polymer that has been irradiated below its melting point with ionizing radiation contains cross-links as well as long-lived trapped free radicals. These free radicals react with oxygen over the long-term and result in the embrittlement of the polymer through oxidative degradation. The free radicals can be eliminated by any method, which gives this result, including, for example, heating the polymer to above its melting point to permit the free radicals to recombine.

References herein to the melting point of a polymer refer to the peak melting temperature measured in DSC.

1. Polymer Materials

The selective, controlled manipulation of polymers using irradiation chemistry can be achieved, in one aspect, by the selection of the polymer to be irradiated. The properties of the polymer, such as density, molecular weight, crystallinity, and/or crosslink density contribute to the properties of the irradiated polymer and can be selected and combined to yield an irradiated polymer with a desired set of properties.

a. Polymers

Any suitable polymer may be used in accordance with the present invention. Suitable polymers include those that are biocompatible and biostable. Exemplary polymers include types of polyethylenes.

Polyethylene polymers are particularly suitable for use with the present invention. Suitable polyethylenes include, but are not limited to, ultra high molecular weight polyethylene (UHMWPE), high-density polyethylene (HDPE), low density polyethylene (LDPE), linear low density polyethylene (LDPE), each of which have been defined above. Additionally, the invention can be used with ultra low density polyethylene (ULDPE), very low density polyethylene (VLDPE), The VLDPE and ULDPE are defined as a polyethylene with a density less than about 0.913 g/cm³. Such polymers are known to those of skill in the art and available from commercial source. For instance ULDPE and VLDPE are available from Dow Chemical under the tradename of Attane and from Nova Chemical under the tradename of Sclair.

It also is suitable to use polymer alloys in accordance with the present invention. As used herein, a polymer alloy is a blend of two or more polymers with the identical repeat unit with differences in their molecular structures. The differences could be in the molecular weights and/or degrees of branching of the polymers in some instances leading to differences in their physical properties such as density. Suitable alloys include polyethylene/polyethylene alloys in which the constituents of the alloy have different molecular weights, different densities, and/or different degrees of branching. For instance, an alloy made out of at least two or more of the following polyethylenes: LDPE, HDPE, LLDPE, ULDPE, VLDPE and other polyethylenes. In a polymer alloy the constituent polymers could be either miscible or immiscible. The polymer alloys are known to co-crystallize during crystallization. In some alloys the crystallization of the constitutive polymers occur separately to form their respective crystalline structures.

2. Methods and Sequence of Irradiation

The selective, controlled manipulation of polymers and polymer alloys using radiation chemistry can, in another aspect, be achieved by the selection of the method by which the polymer is irradiated. The particular method of irradiation employed, either alone or in combination with other aspects of the invention, such as the polymer or polymer alloy chosen, contribute to the overall properties of the irradiated polymer.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth and extensive oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in a more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm³, which leads to the penetration of about 1 cm with a beam energy of 2–3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

a. Irradiation Methods (i) Irradiation in the Molten State (IMS)

Melt-irradiation, or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours. For UHMWPE, the polymer may be heated to a temperature between about 145° C. and about 230° C., preferably about 150° C. to about 200° C.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in a more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2–3 MeV and about 4 cm with a beam energy of 10 MeV. The penetration of e-beam is known to increase slightly with increased irradiation temperatures. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

The temperature of melt-irradiation for a given polymer depends on the DSC (measured at a heating rate of 10° C./min during the first heating cycle) peak melting temperature ("PMT") for that polymer. In general, the irradiation temperature in the IMS process is about 2° C. higher than the PMT, more preferably between about 2° C. and about 20° C. higher than the PMT, and most preferably between about 5° C. and about 10° C. higher than the PMT.

The total dose of irradiation also may be selected as a parameter in controlling the properties of the irradiated polymer. In particular, the dose of irradiation can be varied to control the degree of cross-linking and crystallinity in the irradiated polymer. The total dose may range from about 0.1 Mrad to as high as the irradiation level where the changes in the polymer characteristics induced by the irradiation reach a saturation point. For instance the high end of the dose range could be 20 Mrad for the melt-irradiation of UHMWPE, above which dose level the crosslink density and crystallinity are not appreciably affected with any additional dose. The preferred dose level depends on the desired properties that will be achieved following irradiation. Additionally, the level of crystallinity in polyethylene is a strong function of radiation dose level. See Dijkstra et al., *Polymer* 30: 866–73 (1989). For instance with IMS irradiation, a dose level of about 20 Mrad would decrease the crystallinity level of UHMWPE from about 55% to about 30%. This decrease in crystallinity may be desirable in that it also leads to a decrease in the elastic modulus of the polymer and consequently a decrease in the contact stress when a medical prosthesis made out of the IMS-treated UHMWPE gets in contact with another surface during in vivo use. Lower contact stresses are preferred to avoid failure of the polymer through, for instance, subsurface cracking, delamination, fatigue, etc. The increase in the crosslink density is also desirable in that it leads to an increase in the wear resistance of the polymer, which in turn reduces the wear of the medical prostheses made out of the crosslinked polymer and substantially reduces the amount of wear debris formed in vivo during articulation against a counterface. In general, the melt-irradiation and subsequent cooling will lead to a decrease in the crystallinity of the irradiated polymer.

Exemplary ranges of acceptable total dosages are disclosed in greater detail in U.S. Pat. No. 5,879,400 and International Application WO 97/29793. For example, preferably a total dose of about or greater than 1 MRad is used. More preferably, a total dose of greater than about 20 Mrad is used.

In electron beam IMS, the energy deposited by the electrons is converted to heat. This primarily depends on how well the sample is thermally insulated during the irradiation. With good thermal insulation, most of the heat generated is not lost to the surroundings and leads to the adiabatic heating of the polymer to a higher temperature than the irradiation temperature. The adiabatic heating could also be induced by using a high enough dose rate to minimize the heat loss to the surroundings. In some circumstance, adiabatic heating may be detrimental to the sample that is being irradiated. Gaseous by-products, such as hydrogen gas when PE is irradiated, are formed during the irradiation. During irradiation, if the adiabatic heating is rapid and high enough to cause rapid expansion of the gaseous by-products, and thereby not allowing them to diffuse out of the polymer, the polymer may cavitate. The cavitation is not desirable in that it leads to the formation of defects (such as air pockets, cracks) in the structure that could in turn adversely affect the mechanical properties of the polymer and in vivo performance of the device made thereof.

The adiabatic temperature rise depends on the dose level, level of insulation, and/or dose rate. The dose level used in the irradiation stage is determined based on the desired properties. In general, the thermal insulation is used to avoid cooling of the polymer and maintaining the temperature of the polymer at the desired irradiation temperature. Therefore, the adiabatic temperature rise can be controlled by determining an upper dose rate for the irradiation. For instance for the IMS of UHMWPE the dose rate should be less than about 5 Mrad/pass (only applicable for the e-beam and not gamma as gamma is inherently a low dose rate process). These considerations for optimization for a given polymer of a given size are readily determined by the person of skill in view of the teachings contained herein.

In embodiments of the present invention in which electron radiation is utilized, the energy of the electrons can be varied to alter the depth of penetration of the electrons, thereby controlling the degree of crosslinking and crystallinity following irradiation. The range of suitable electron energies is disclosed in greater detail in International Application WO 97/29793. In one embodiment, the energy is about 0.5 MeV to about 12 MeV. In another embodiment the energy is about 1 MeV to 10 MeV. In another embodiment, the energy is about 10 MeV.

(ii) Cold Irradiation (CIR)

Cold irradiation is described in detail in WO 97/29793. In the cold irradiation process, a polymer is provided at room temperature or below room temperature. Preferably, the temperature of the polymer is about 20° C. Then, the polymer is irradiated. In one embodiment of cold irradiation, the polymer may be irradiated at a high enough total dose and/or at a fast enough dose rate to generate enough heat in the polymer to result in at least a partial melting of the crystals of the polymer.

Gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in a more limited dose penetration depths, but requires less time and, therefore, reduces the risk of extensive oxidation. Accordingly, gamma irradiation or electron irradiation may be used based upon the depth of penetration preferred, time limitations and tolerable oxidation levels.

The total dose of irradiation may be selected as a parameter in controlling the properties of the irradiated polymer. In particular, the dose of irradiation can be varied to control the degree of cross-linking and crystallinity in the irradiated polymer. The preferred dose level depends on the molecular weight of the polymer and the desired properties that will be achieved following irradiation. For instance, to achieve maximum improvement in wear resistance using UHMWPE and the WIAM (warm irradiation and adiabatic melting) or CISM (cold irradiation and subsequent melting) processes, a radiation dose of about 10 Mrad is suggested. To achieve maximum improvement in wear resistance using LDPE and LLDPE, a dose level greater than about 10 Mrad is suggested. In general, increasing the dose level with CIR would lead to an increase in wear resistance. If the CIR is carried out without post-irradiation melt-annealing, the crystallinity and elastic modulus of the polymer would increase. Following melt-annealing, however, these would decrease to values lower than those prior to irradiation.

Exemplary ranges of acceptable total dosages are disclosed in greater detail in International Application WO 97/29793. In the embodiments below, UHMWPE is used as the starting polymer. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 Mares or about 15 Mares.

Other exemplary CIR dose levels for various polymers:

| | CIR Dose | | |
| --- | --- | --- | --- |
| POLYMER | Preferred | More preferred | Most preferred |
| LDPE | 0.5–100 | 5–50 | 20 |
| LLDPE | 0.5–100 | 5–50 | 20 |
| ULDPE | 0.5–1000 | 5–300 and 10–200 | 100 |
| VLDPE | 0.5–1000 | 5–300 and 10–200 | 150 |
| HMWPE | 0.5–100 | 5–50 | 20 |
| UHMWPE | 0.5–100 | 5–50 | 15 |
| HDPE | 0.5–100 | 5–50 | 30 |

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. A preferred electron energy for maximum penetration is about 10 MeV, which is commercially available through vendors such as Studer (Daniken, Switzerland) or E-Beam Services (New Jersey, USA). The lower electron energies may be preferred for embodiments where a surface layer of the polymer is preferentially crosslinked with gradient in crosslink density as a function of distance away from the surface.

(iii) Warm Irradiation (WIR)

Warm irradiation is described in detail in WO 97/29793. In the warm irradiation process, a polymer is provided at a temperature above room temperature and below the melting temperature of the polymer. Then, the polymer is irradiated. In one embodiment of warm irradiation, which has been termed "warm irradiation adiabatic melting" or "WIAM" the polymer may be irradiated at a high enough total dose and/or a high enough dose rate to generate enough heat in the polymer to result in at least a partial melting of the crystals of the polymer.

The polymer may be provided at any temperature below its melting point and above room temperature. The temperature selection depends on the specific heat and the enthalpy of melting of the polymer and the total dose level that will be used. The equation provided in International Application WO 97/29793 may be used to calculate the preferred temperature range with the criterion that the final temperature of polymer immediately following the irradiation is not significantly above the melting point. Preheating of the polymer to the desired temperature may be done in an inert or non-inert environment.

Exemplary ranges of acceptable total dosages are disclosed in greater detail in International Application WO 97/29793. In one embodiment, the UHMWPE is preheated to about 20° C. to about 135° C. In one embodiment of WIAM, the UHMWPE is preheated to about 100° C. to just below the melting temperature of the polymer. In another embodiment of WIAM, the UHMWPE is preheated to a temperature of about 100° C. to about 135° C. In yet other embodiments of WIAM, the polymer is preheated to about 120° C. or about 130° C.

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is preheated to about 90° C. In another embodiment, the polymer is heated to about 100° C. In another embodiment, the polymer is preheated to about 30° C. below PMT and 2° C. below PMT. In another embodiment, the polymer is preheated to about 12° C. below PMT.

In the WIAM embodiment of WIR, the temperature of the polymer following irradiation is at or above the melting temperature of the polymer. Exemplary ranges of acceptable temperatures following irradiation are disclosed in greater detail in International Application WO 97/29793. In one embodiment, the temperature following irradiation is about PMT to about 200° C. In another embodiment, the temperature following irradiation is about 145° C. to about 190° C. In yet another embodiment, the temperature following irradiation is about 146° C. to about 190° C. In still another embodiment, the temperature following irradiation is about 150° C.

In WIR, gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in a more limited dose penetration depths, but requires less time and, therefore, reduces the risk of extensive oxidation. Accordingly, gamma irradiation or electron irradiation may be used based upon the depth of penetration preferred, time limitations and tolerable oxidation levels. In the WIAM embodiment of WIR, electron radiation is used.

The total dose of irradiation may also be selected as a parameter in controlling the properties of the irradiated polymer. In particular, the dose of irradiation can be varied to control the degree of cross-linking and crystallinity in the irradiated polymer. Exemplary ranges of acceptable total dosages are disclosed in greater detail in International Application WO 97/29793.

The dose rate of irradiation also may be varied to achieve a desired result. The dose rate is a prominent variable in the WIAM process. In the case of WIAM irradiation of UHMWPE, higher dose rates would provide the least amount of reduction in toughness and elongation at break. The preferred dose rate of irradiation would be to administer the total desired dose level in one pass under the electron-beam. One can also deliver the total dose level with multiple passes under the beam, delivering a (equal or unequal) portion of the total dose at each time. This would lead to a lower effective dose rate.

Ranges of acceptable dose rates are exemplified in greater detail in International Application WO 97/29793. In general, the dose rates will vary between 0.5 Mrad/pass and 15 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially crosslinked with gradient in crosslink density as a function of distance away from the surface.

(iv) Subsequent Melting (SM)—Substantial Elimination of Detectable Residual Free Radicals Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped at crystalline lamellae surfaces Kashiwabara, H. S. Shimada, and Y. Hori, *Free Radicals and Crosslinking in Irradiated Polyethylene*, Radiat. Phys. Chem., 1991, 37(1): p. 43–46; leading to oxidation-induced instabilities in the long-term. Jahan, M. S. and C. Wang, *Combined Chemical and Mechanical Effects on Free radicals in UHMWPE Joints During Implantation*, Journal of Biomedical Materials Research, 1991, 25: p. 1005–1017; Sutula, L. C., et al., Impact of gamma sterilization on clinical performance of polyethylene in the hip", *Clinical Orthopedic Related Research*, 1995, 3129: p. 1681–1689. The elimination of these residual, trapped free radicals through melt annealing is, therefore, desirable in precluding long-term oxidative instability of the polymer. Jahan M. S. and C. Wang, "Combined chemical and mechanical effects on free radicals in UHMWPE joints during implantation", *Journal of Biomedical Materials Research*, 1991, 25: p. 1005–1017; Sutula, L. C., et al., "Impact of gamma sterilization on clinical performance of polyethylene in the hip", *Clinical Orthopedic Related Research*, 1995, 319: p. 28–4.

If there are residual free radicals remaining in the material, these may be reduced to substantially undetectable levels, as measured by electron spin resonance or other tests, through annealing of the polymer above the melting point of the polymeric system used. The melt annealing allows the residual free radicals to recombine with each other. If for a given system the preform does not have substantially any detectable residual free radicals following irradiation, then a melt annealing step may be omitted. Also, if for a given system the concentration of the residual free radicals are low enough to not lead to degradation of device performance, the melt annealing step may be omitted. In some of the lower molecular weight and lower density polyethylenes, the residual free radicals may recombine with each other even at room temperature over short periods of time, e.g. few hours to few days, to few months. In such cases, the subsequent melt-annealing may be omitted if the increased crystallinity and modulus resulting from the irradiation is preferred. Otherwise, the subsequent melt-annealing may be carried out to decrease the crystallinity and modulus. In the case where melt annealing is omitted, the irradiated preform can be directly machined into the final medical device.

The reduction of residual free radicals to substantially undetectable levels is particularly important if the polymer is used in the manufacture of any of the medical devices, such as orthopedic devices.

The reduction of free radicals to point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT)

and degradation temperature ($T_d$) of the polymer, more preferably between about 3° C. above PMT and $T_d$, more preferably between about 10° C. above PMT and 50° C. above PMT, more preferably between about 10° C. and 12° C. above PMT and most preferably about 15° C. above PMT.

Preferably, for UHMWPE the polymer is heated to a temperature of about 137° C. to about 300° C., more preferably about 140° C. to about 300° C., more preferably yet about 140° C. to about 190° C., more preferably yet about 145° C. to about 300° C., more preferably yet about 145° C. to about 190° C., more preferably yet about 146° C. to about 190° C., and most preferably about 150° C. Preferably, the temperature in the heating step is maintained for about 0.5 minutes to about 24 hours, more preferably about 1 hour to about 3 hours, and most preferably about 2 hours. The heating can be carried out, e.g., in air, in an inert gas, e.g., nitrogen, argon or helium, in a sensitizing atmosphere, e.g., acetylene, or in a vacuum. It is preferred that for the longer heating times, that the heating be carried out in an inert gas or under vacuum to avoid in-depth oxidation.

In certain embodiments, there may be a tolerable level of residual free radicals in which case, the post-irradiation annealing can also be carried out below the melting point of the polymer.

b. Different Properties of Polymers Irradiated with Different Techniques

The various irradiation techniques described above may be used, either individually or in combination, to yield a polymer with certain desired properties.

Figure 2:
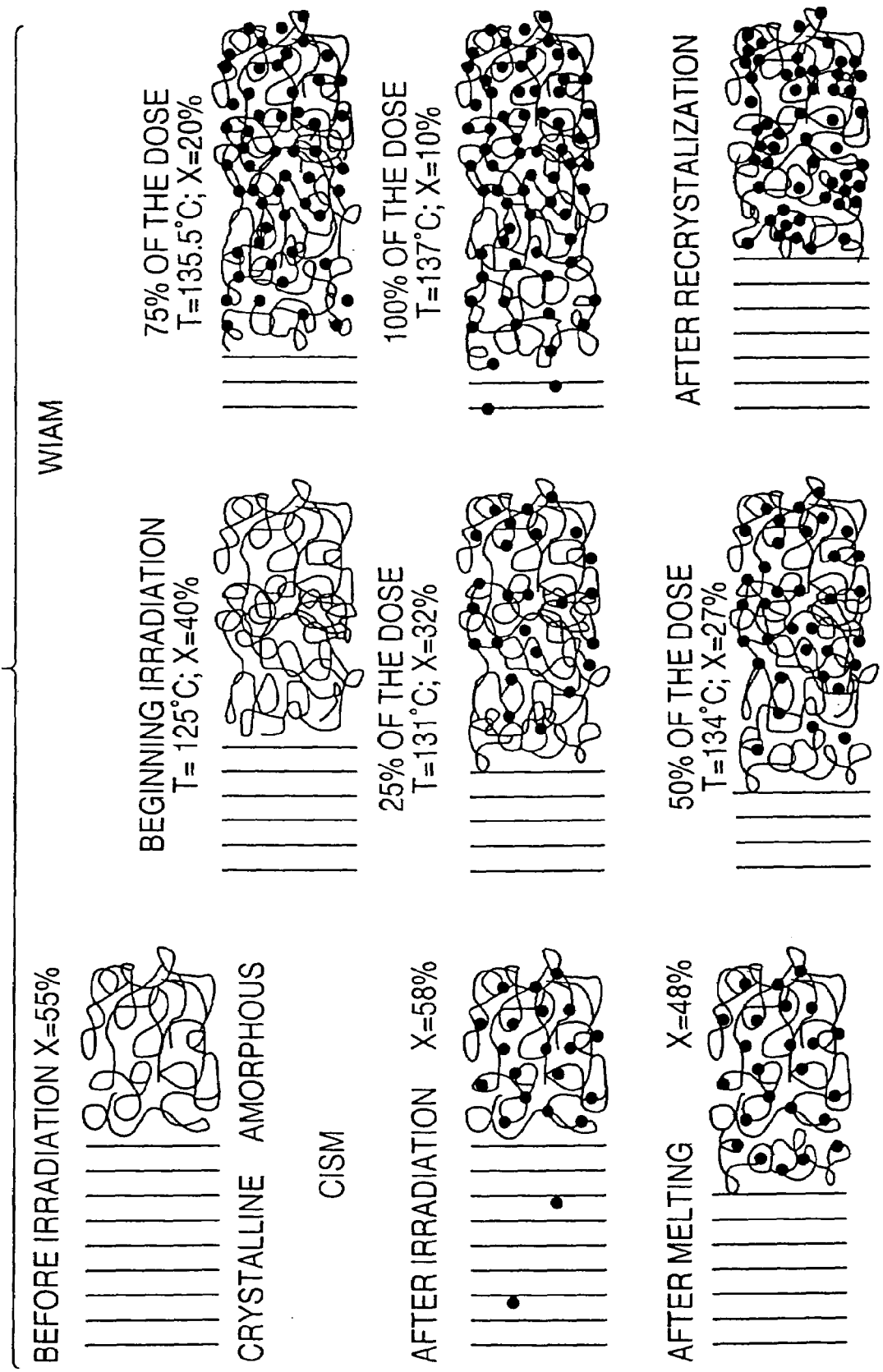
FIG. 2 depicts a postulated molecular morphology evolution in two different irradiation processes, namely CISM and WIAM (defined and described in greater detail below).

In the case of polyethylene, a semi-crystalline polymer with around 50% crystallinity, the irradiation method selected will significantly contribute to the properties of the irradiated polymer. When polyethylene is irradiated, even though the radiolytic reactions take place throughout the structure, the crosslinks form principally in the amorphous phase where there is limited hindrance to molecular mobility. See McGinniss, V., *Crosslinking with radiation, in Polymer Handbook*, J. Brandrup and E. H. Immergut, Eds. (1989); Dole, M., "Crosslinking and crystallinity in irradiated polyethylene," *Polym.-Plast. Technol. Eng.*, 13(1): 41–46 (1979). Therefore, the IMS process leads to the uniform crosslinking of all molecular chains by eliminating the crystals through melting, while the CI-SM process leads to a non-uniform crosslinking only in 50% of the chains. In the WIAM process, the polyethylene is heated to below its melting point to a crystallinity level of 40% and irradiated at a high dose rate. During irradiation, due to the heat generated by the irradiation, which follows a thermodynamic equilibrium, generated by the high dose rate more crystals are melted and made available for crosslinking. Certain chains are present for the complete irradiation and receive the full dose level, while others only receive a fraction of the dose left from the time they are melted. Consequently, the crosslink density distribution of the WIAM is highly non-statistical compared to the CI-SM and IMS (see FIG. 2 for a schematic description). In fact, the WIAM-treated polyethylene always exhibits at least two melting peaks indicative of at least a two-phase structure. WIAM treated PE that has a final temperature following irradiation that is lower than the melting temperature of the polymer will exhibit three melting peaks. If such polymer is subjected to subsequent melting, the three peaks will resolve into two. WIAM treated PE that has a final temperature following irradiation that is at or above the melting temperature of the polymer will exhibit two melting peaks. In contrast, there is only one melting peak with CISM and IMS treated PE. As a result, some material properties of the IMS, CISM, and WIAM crosslinked polyethylenes differ significantly. Table I shows some of these expected changes in UHMWPE.

TABLE I

| | IMS | | CISM | | WIAM | |
|---|---|---|---|---|---|---|
| | Low dose | High dose | Low dose | High dose | Low dose | High dose |
| Modulus | ↓ | ↓ | ↓ | → | ↓ | → |
| Yield Stress | ↓ | ↓ | ↓ | → | ↓ | → |
| Yield Strain | ↓ | → | ↓ | → | ↓ | → |
| Ultimate Stress | ↓ | ↓ | ↓ | → | ↓ | → |
| Ultimate Strain | ↓ | ↓ | ↓ | → | ↓ | → |
| Creep Resistance | ↓ | ↓ | ↓ | → | ↓ | ↑ |
| Viscoelasticity☐ | ↓ | ↓ | ↓ | ↓ | → | → |
| Toughness | ↓ | ↓ | ↓ | ↓ | → | → |

↓: Decrease
→: Little decrease or significiantly no change
↑: Increase
Low dose ~2–3 Mrad
High dose >>4 Mrad The WIAM technique is not expected to alter the viscoelasticity of the polymer even at high dose levels, which is a significant drawback of the other techniques as shown in Table I.

c. Sequence of Irradiation

In embodiments in which more than one method of irradiation is utilized, the sequence of the irradiation methods may be set to achieve a particular result. In certain embodiments, the WIAM treatment of the polymer may lead to bubbles and cracks due to low bulk strength of the polymer (for instance some of the lower molecular weight polyethylenes). Therefore, one can use the CIR (with or without subsequent melting) at a low dose level (5–10 Mrad) to increase the bulk strength of the polymer, then subsequently use the WIAM process to achieve the desired properties. Other sequences will become apparent to the skilled person in view of the teachings contained herein.

3. Preferential Irradiation Shielding

The selective, controlled manipulation of polymers using radiation chemistry can, in another aspect, be achieved by preferential irradiation shielding. By using a shield or shields made of selected materials, selected thicknesses, selected geometry's, selected areas and utilization of the shields in a selected order, the overall properties of the irradiated polymer may be controlled and tailored to achieve a desired result, particularly in view of alterations that can be made in the type of irradiation, the irradiation dose, dose rate and exposure time and temperature, as well as the methodology used (for example, IMS, WIR, CIR, CIR-SM and WIAM).

a. Shield Material

The irradiation shield may be made from any material that will at least shield in part polymer from the irradiation. Exemplary materials include ceramics, metals, and glass. Suitable ceramics include alumina and zirconia. Suitable metals include aluminum, lead, iron, and steel. Polymers also may be used as shields.

b. Shield Geometry's and Order

An irradiation shield may be provided in any shape, cross-section, or thickness.

It is well known in the art that the thickness of the shield will contribute to the ability of the material to shield the irradiation. Accordingly, the thickness of the shield can be selected depending upon the extent of shielding that is desired in the shielded portion. In this manner, the depth of irradiation penetration can be controlled, or a total shielding of irradiation of the covered areas can be achieved. The iso-dose penetration (defined as the depth at which the dose equals that at the e-beam incidence surface) and the dose-depth penetration profile depend on the energy of the electrons used. See Section 6a.

Thus, effect of irradiation and shielding can be controlled through the materials used in the shield, the thickness of the shield (constant or variable), the extent to which the shield covers the area of the material being irradiated (full or partial), the order of shielding and irradiation, the type and extent of irradiation, and polymer selection.

c. Complete Coverage Shielding

UHMWPE (GUR 1050) was covered by aluminum shield of varying thicknesses (1, 3, 5, 7, 9, 11, 13, 15 mm) and irradiated either at room temperature or at 125° C. The irradiation was carried out at E-Beam Services (Cranbury, N.J.) using the 10/50 Impela linear electron accelerator operated at 10 MeV and 50 kW. To determine the penetration profile of the effects of e-beam, spatial variation in the trans-vinylene content in the irradiated UHMWPE specimens was determined. The GUR 1050 UHMWPE has no detectable trans-vinylene unsaturations. The ionizing radiation, e-beam in the present case, leads to the formation of trans-vinylene unsaturations, the content of which varies linearly with absorbed radiation dose.

Figure 3:
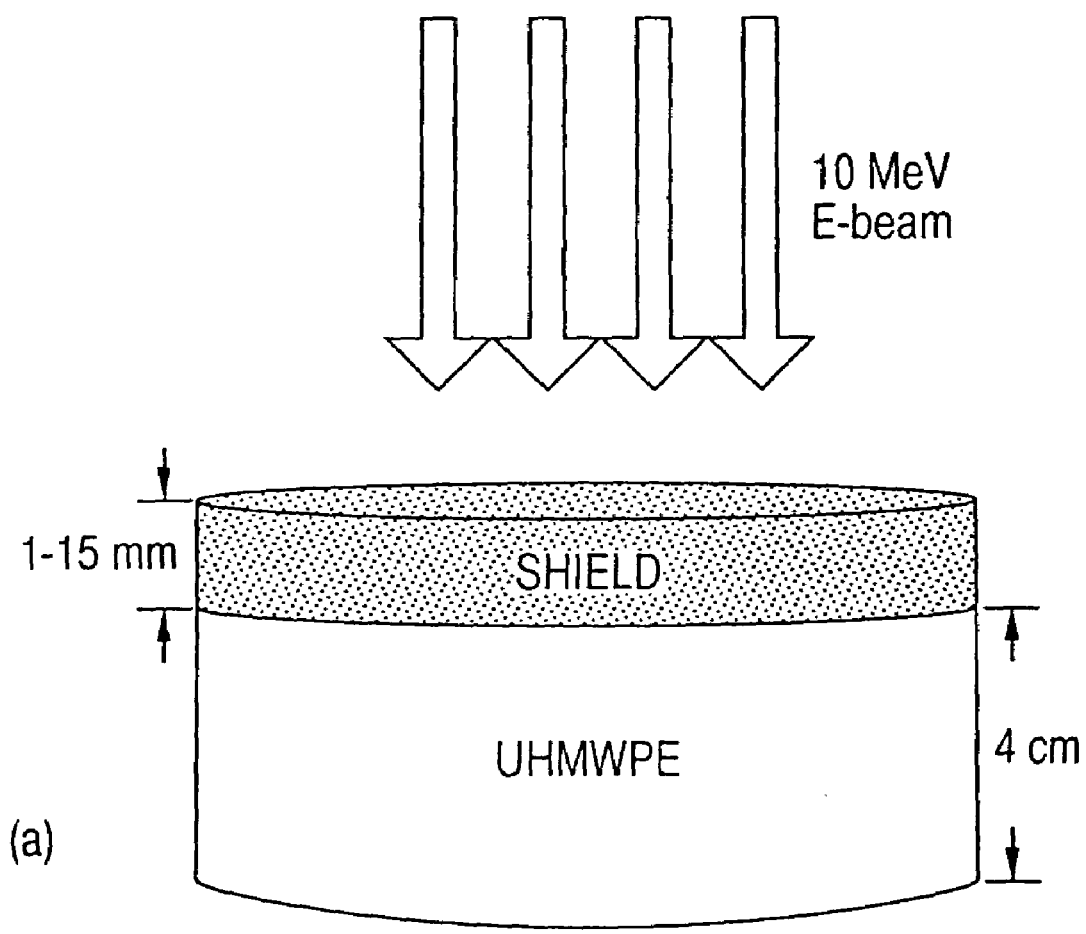
FIG. 3 depicts a schematic of a complete coverage shield covering a UHMWPE construct.
Figure 4:
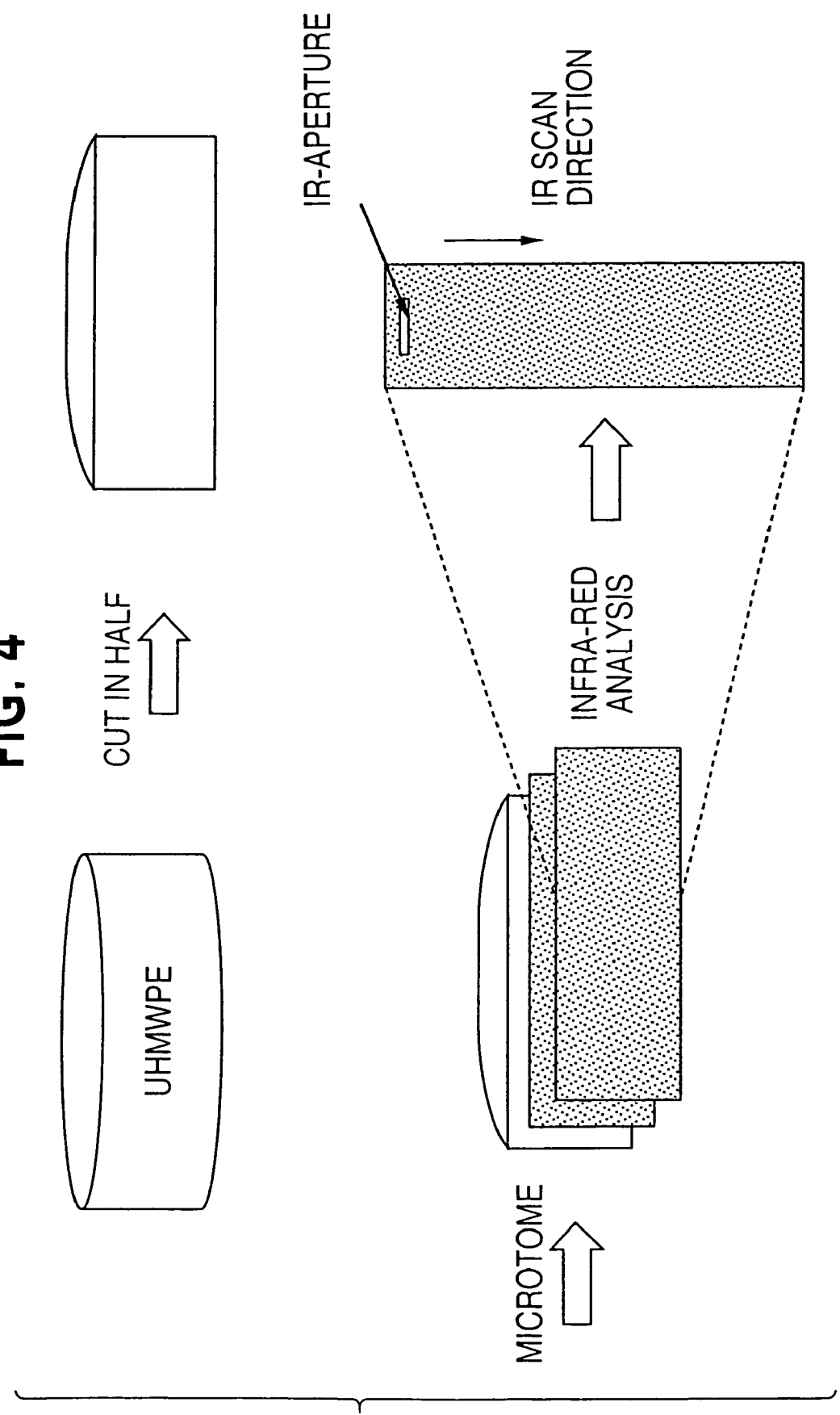
FIG. 4 depicts the construct of FIG. 3 that has been bisected for microtoming.

FIG. 3 shows a schematic of the shield UHMWPE construct. Following irradiation, the irradiated UHMWPE construct was machined in half and microtomed as shown in FIG. 4. The microtomed thin section was then analyzed using a BioRad UMA 500 infra-red microscope with an aperture size of 100 µm by 50 µm as a function of depth away from the shield/UHMWPE interface at 1 mm increments. Each individual infra-red spectra was then analyzed by normalizing the area under the trans-vinylene vibration at 965 cm$^{-1}$ to the that under the 1900 cm$^{-1}$ after subtracting the respective baselines. The value obtained, that is the trans-vinylene index (TVI), is directly proportional to the absorbed radiation dose level.

The following equation was used:

$$TVI = \frac{\int_{950}^{980} A(w)\,dw - B_1}{\int_{1850}^{1985} A(w)\,dw - B_2}$$

$$B_1 = \frac{[A(980) + A(950)](980 - 950)}{2}$$

$$B_2 = \frac{[A(1850) + A(1985)](1985 - 1880)}{2}$$

where A(w) is the infra-red absorbance measured at wave number, w, $B_1$ is the area under the baseline of the trans-vinylene vibration and $B_2$ is that of the baseline under the reference (1900 cm$^{-1}$) vibration.

Figure 5:
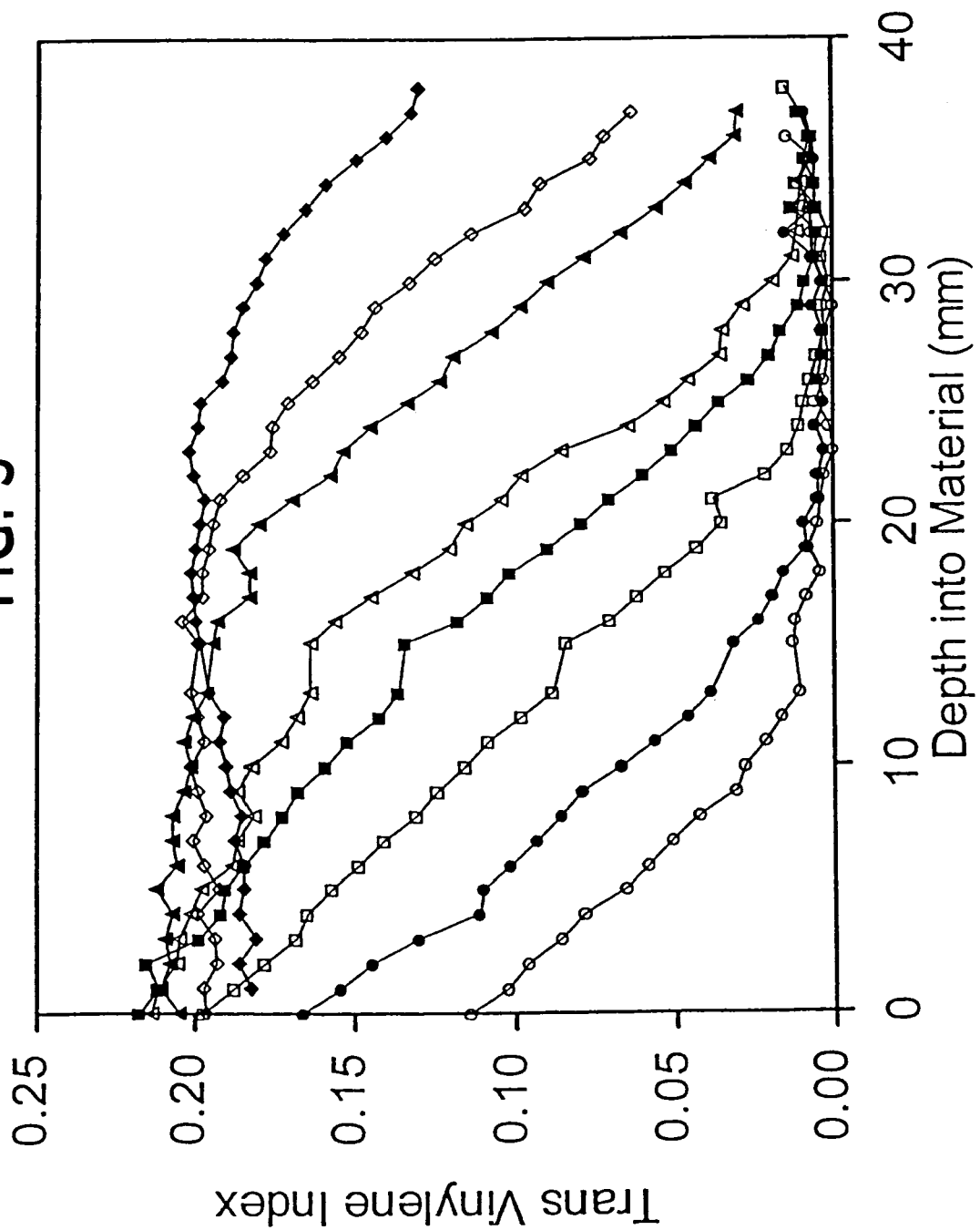
FIG. 5 shows the variation of the trans vinylene index as a function of distance for UHMWPE irradiated at room temperature.
Figure 6:
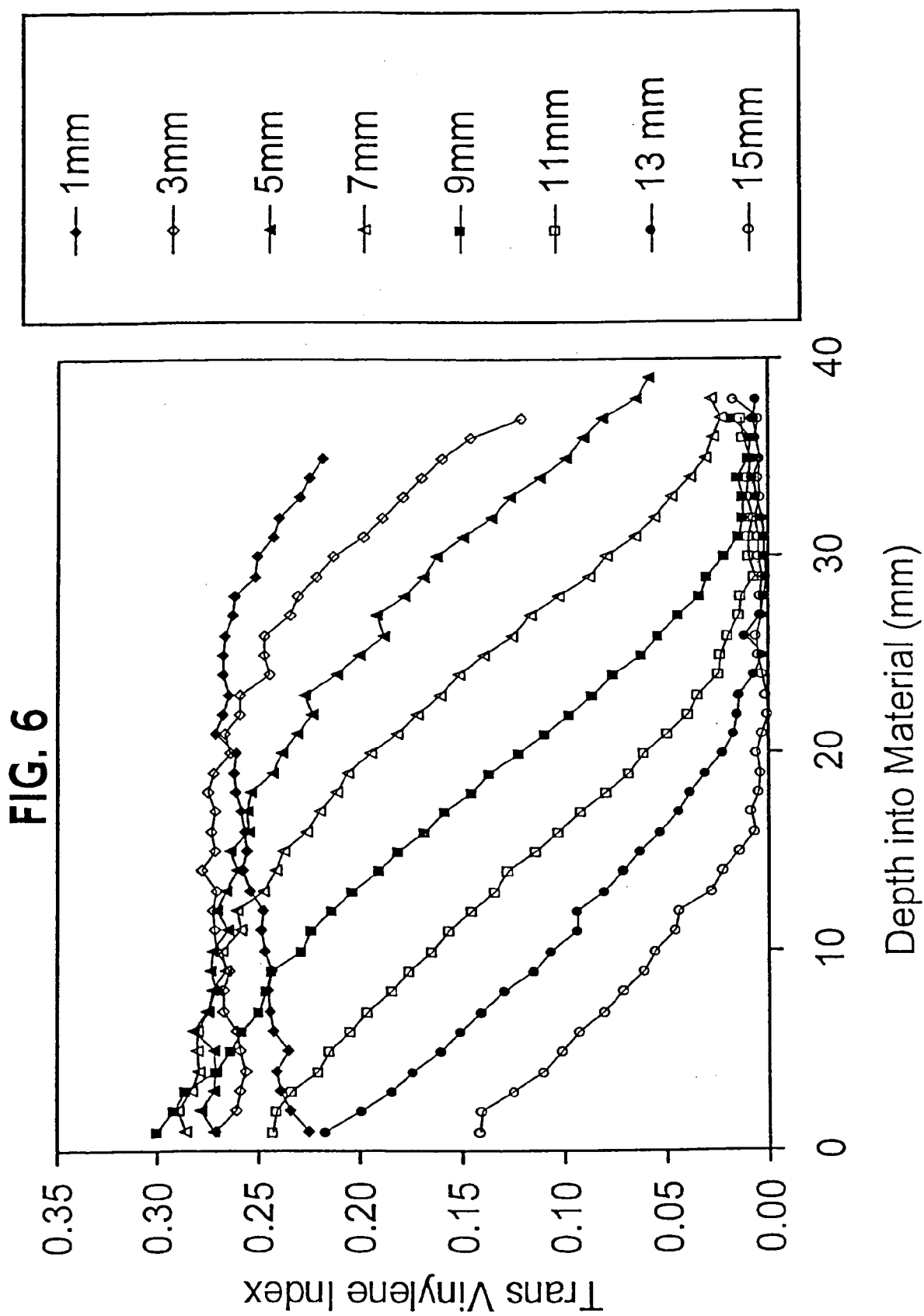
FIG. 6 shows the variation of the trans vinylene index as a function of distance for UHMWPE irradiated at 125° C.
Figure 7:
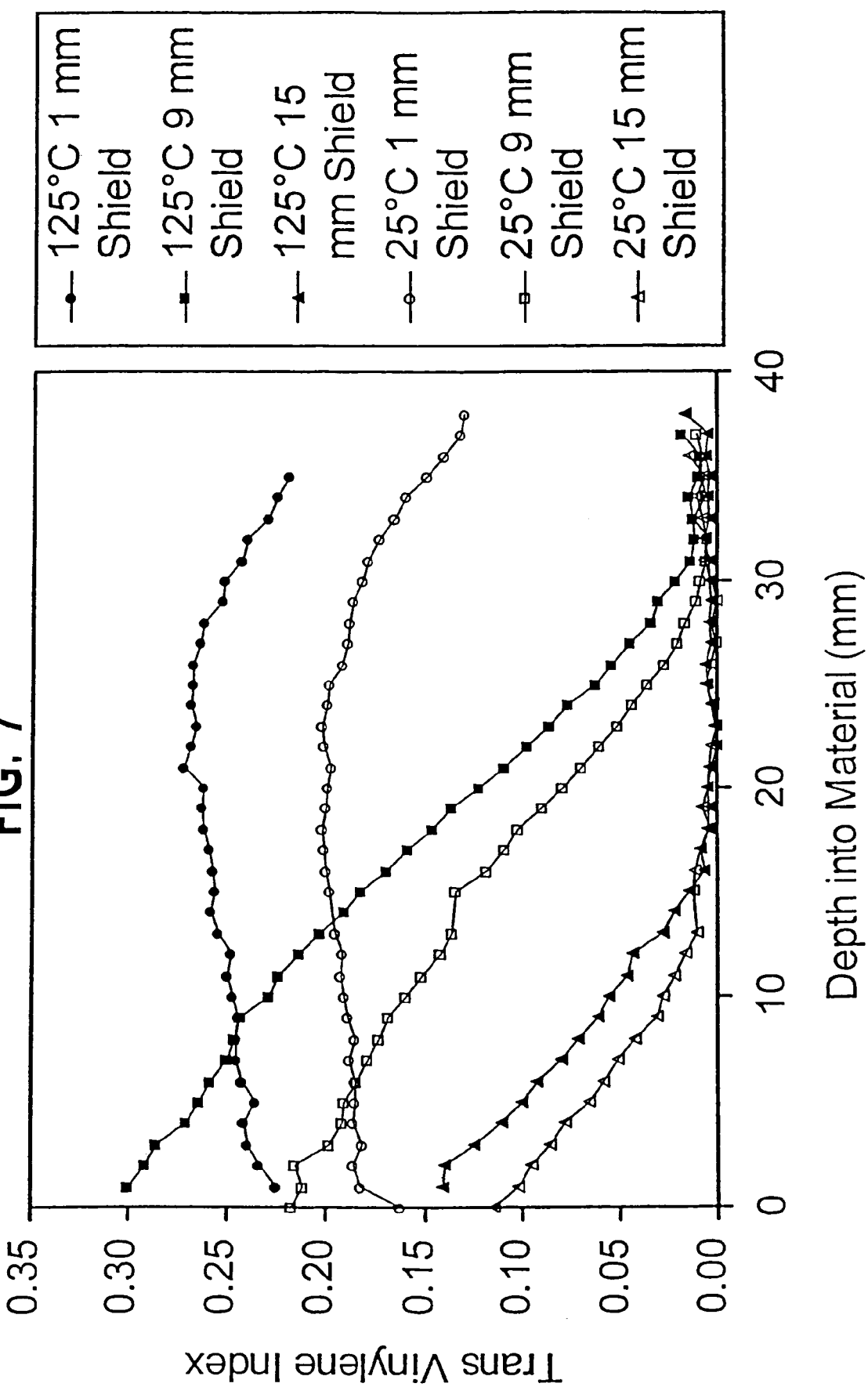
FIG. 7 shows the variation of the trans vinylene index as a function of distance for UHMWPE irradiated at 2 different temperature (25° C. and 125° C.) and different complete (that is, full) coverage shield thicknesses (1 mm, 9 mm, and 15 mm).

FIG. 5 shows the variation of TVI in room temperature irradiated UHMWPE as a function of distance away from the shield/UHMWPE interface for different shield thicknesses. FIG. 6 shows the same for the UHMWPE that was irradiated at 125° C. The figures clearly show that the penetration of the effects of e-beam can be controlled by placing an aluminum shield and by varying its thickness. The temperature at which the irradiation is being carried can also be used to change the profile of the beam penetration. This is illustrated in FIG. 7 where the variation in TVI with depth is presented for three different shield thicknesses (1, 9, and 15 mm) and two irradiation temperatures (25° C. and 125° C.).

d. Paitial Coverage Shielding

Figure 8:
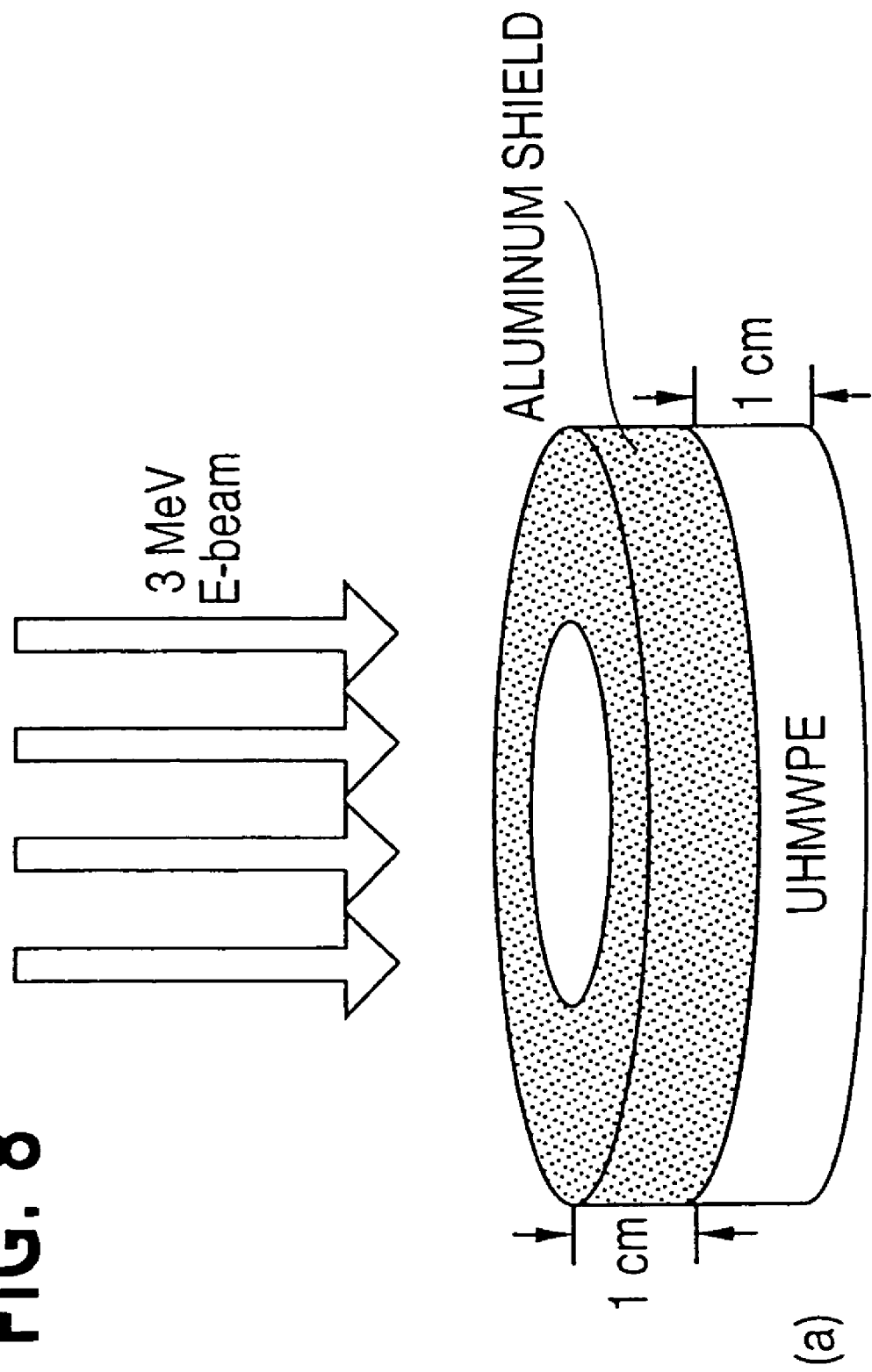
FIG. 8 depicts a UHMWPE construct covered with a 1 cm thick aluminum partial shield (hole in center).

UHMWPE (GUR 1050) was covered by a 1 cm thick aluminum shield with a round opening in the center, as shown in FIG. 8. The UHMWPE/shield construct was then irradiated at 150° C. using the Van de Graaf generator at the High Voltage Research Laboratories of Massachusetts Institute of Technology (Cambridge, Mass.). This partial shielding scheme should lead to the irradiation of the central part of the UHMWPE cylinder. To confirm this, the spatial distribution of the effects of e-beam was determined by measuring the content of trans-vinylene unsaturations as a function of distance away from the side-wall to the center of the UHMWPE disc in the direction perpendicular to the e-beam incidence direction.

The GUR 1050 UHMWPE has no detectable trans-vinylene unsaturations. The ionizing radiation, e-beam in the present case, leads to the formation of trans-vinylene unsaturations, the content of which varies linearly with absorbed radiation dose.

Figure 9:
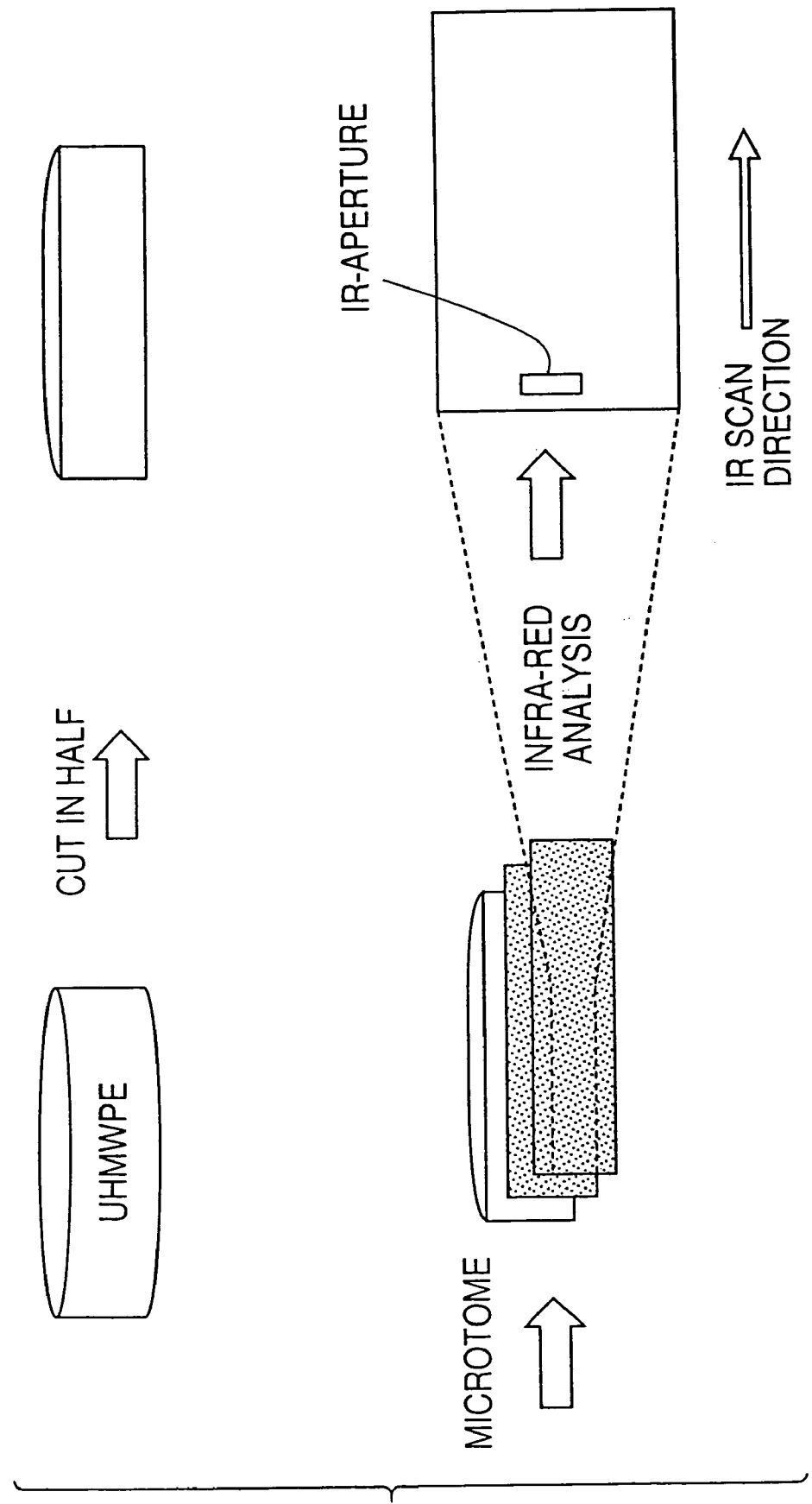
FIG. 9 depicts the construct of FIG. 8 that has been bisected for microtoming.

Following irradiation, the irradiated UHMWPE cylinder was machined in half and microtomed as shown in FIG. 9. The microtomed thin section was then analyzed using a BioRad UMA 500 infra-red microscope with an aperture size of 100 µm by 50 µm as a function of depth away from the sidewall to the center of the irradiated UHMWPE disk at 1 mm increments. Each individual infra-red spectra was then analyzed by normalizing the area under the trans-vinylene vibration at 965 cm$^{-1}$ to the that under the 1900 cm$^{-1}$ after subtracting the respective baselines. The value obtained, that is the trans-vinylene index (TVI), is directly proportional to the absorbed radiation dose level.

The following equation was used:

$$TVI = \frac{\int_{950}^{980} A(w)\,dw - B_1}{\int_{1850}^{1985} A(w)\,dw - B_2}$$

$$B_1 = \frac{[A(980) + A(950)](980 - 950)}{2}$$

$$B_2 = \frac{[A(1850) + A(1985)](1985 - 1880)}{2}$$

where A(w) is the infra-red absorbance measured at wave number, w, $B_1$ is the area under the baseline of the trans-vinylene vibration and $B_2$ is that of the baseline under the reference (1900 cm$^{-1}$) vibration.

Figure 10:
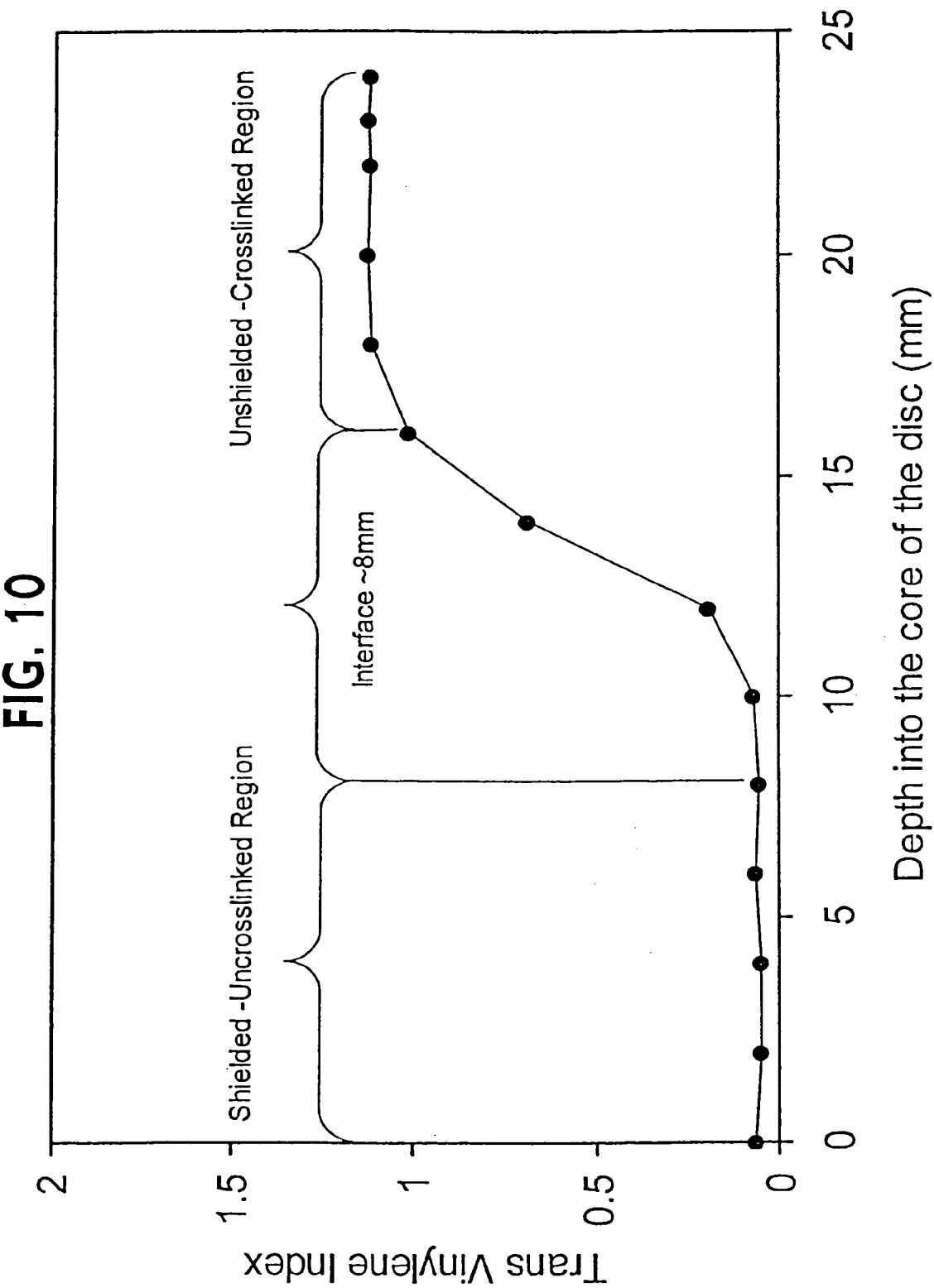
FIG. 10 shows the variation of the trans vinylene index as a function of distance for irradiated UHMWPE.

FIG. 10 shows the variation of TVI in the irradiated UHMWPE as a function of distance away from the sidewall of the shielded and irradiated UHMWPE. Under the shielded region, the TVI level was near zero; while the value under the unshielded region increased, indicating the presence of radiation in this region.

Figure 11:
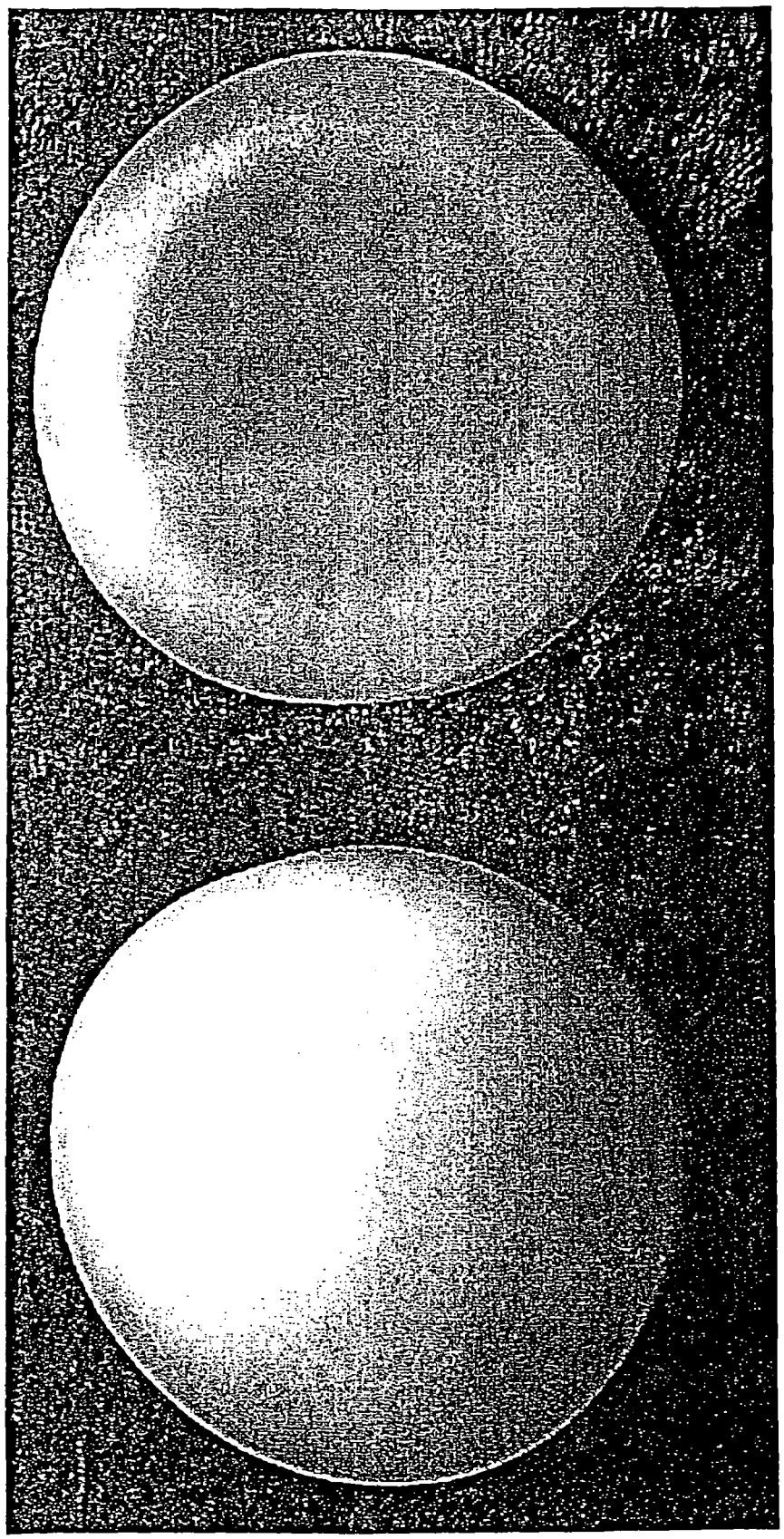
FIG. 11 compares unradiated UHMWPE (panel a) to the partially-shield UHMWPE (panel b) according to FIG. 8.
Figure 13:
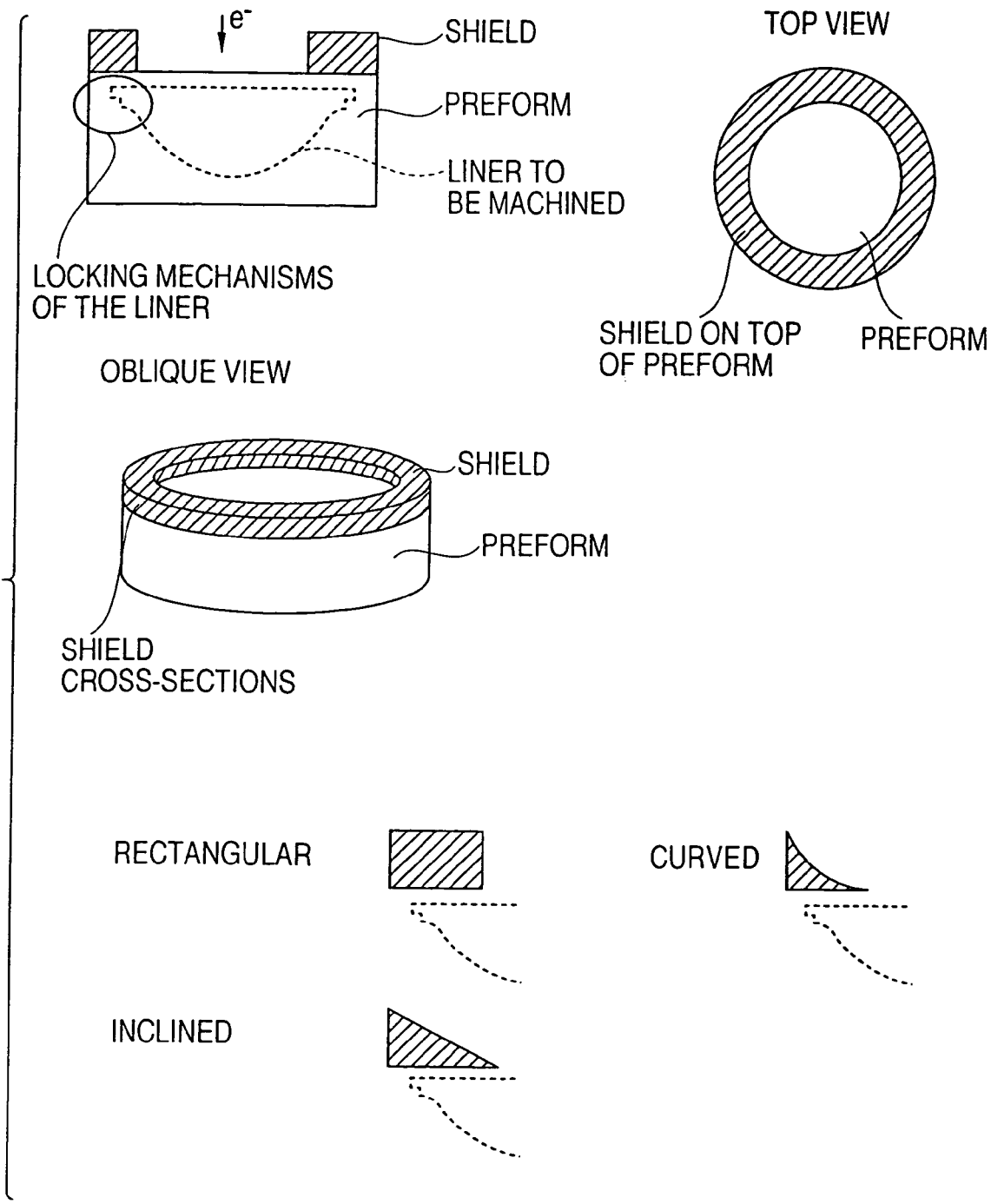
FIG. 13 depicts the use of the present invention in the fabrication of an acetabular liner of a hip prosthesis.

The effect of irradiation with a disc shaped shield on UHMWPE also is illustrated in FIG. 11 where an unirradiated UHMWPE (panel a) and shield-irradiated UHMWPE (panel b) are shown. When the irradiation is carried out above the melting point of UHMWPE, which is the case here, the crystallinity decreases significantly and melt-irradiated UHMWPE becomes more transparent. This transparency is apparent in Figure panel b, in the region where the shield was not covering the UHMWPE disc. The decrease in the crystallinity is also associated with a decrease in modulus. Therefore, one can use the procedure described here to manufacture different shaped UHMWPE with regions of lower modulus for specific medical applications.

The shape and cross-section of the shield also plays an important role in determining the properties of the irradiated polymer. Any shape and cross-section shield, or combination of shapes and cross-sections, may be utilized to achieve a desired cross-link depth and pattern.

Figure 18:
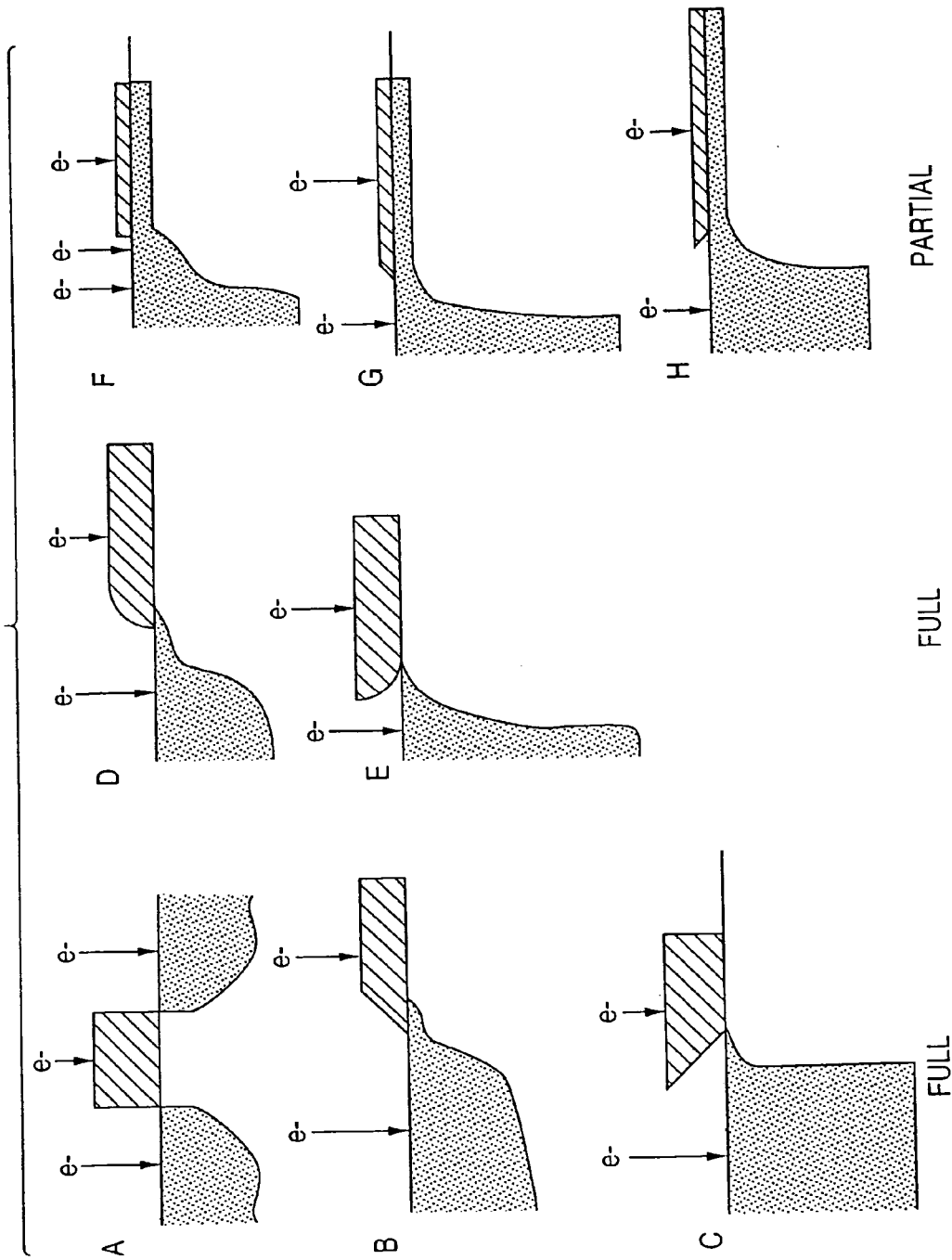
FIG. 18 depicts exemplary shield edge geometry's and the resultant irradiation penetration envelopes. One set of illustrations shows shields that fully block the radiation from the covered area, while the other set of illustrations shows shields that partially block the radiation from the covered area.
Figure 19:
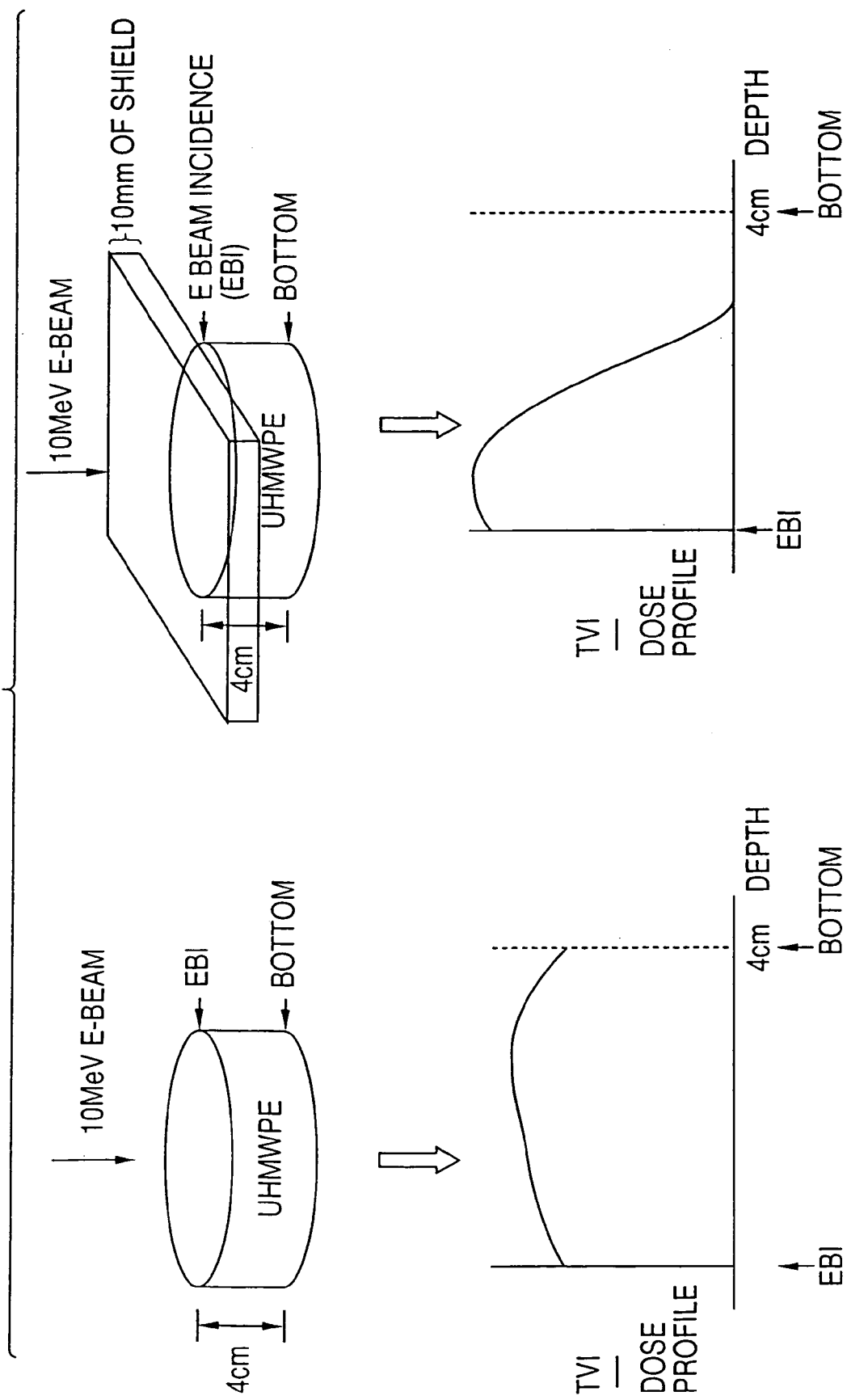
FIG. 19 is an illustration of the effect of a radiation shield on the depth of penetration of electron radiation at 10 MeV.
Figure 20:
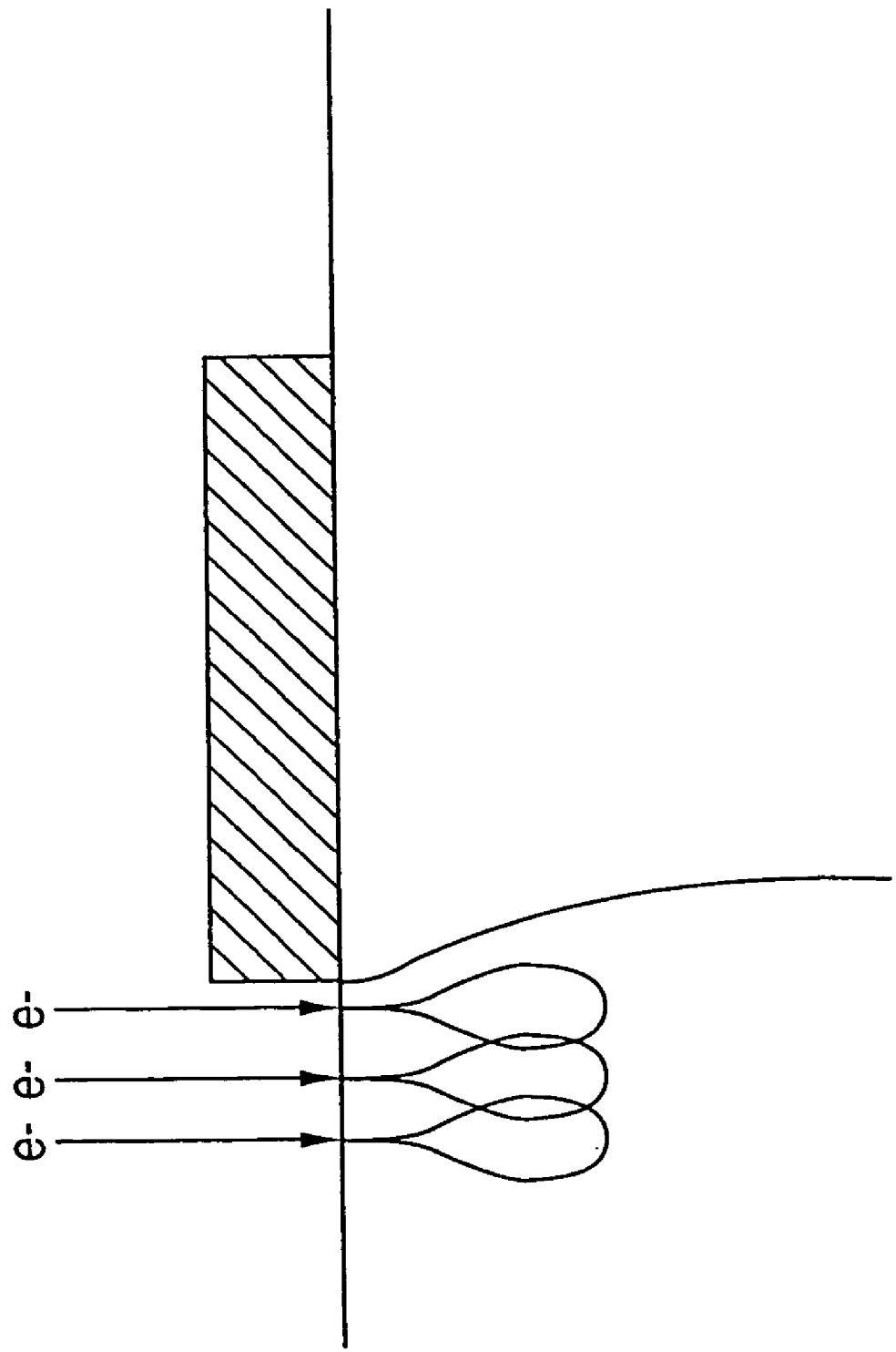
FIG. 20 is a depiction of the "teardrop" electron penetration envelope signature left by electron radiation as it travels through a polymer.

FIG. 18 illustrates some exemplary shield edge geometry's and the hypothesized irradiation penetration envelopes resulting therefrom are shown in FIG. 20. In particular, depiction (A) FIG. 18 show a rectangular cross-section. The cross-link pattern, when there is a full blocking of irradiation, leaves most of the area under the shield uncross-linked. However, there is a portion of the polymer under each edge of the shield that is cross-linked due to the electron penetration envelope. This pattern is the result of the "teardrop" signature left by electron radiation as it travels through the polymer. This signature is depicted in FIG. 20. FIG. 19 illustrates the effect of an irradiation shield on the depth of penetration of electron radiation at 10 MeV.

Depictions (B), (C), (G) and (H) illustrate an inclined or declined cross-section and the resultant cross-linking pattern. Depictions (D) and (E) illustrate a curved cross-section and the resultant cross-linking pattern. Other cross-sections are attainable according to the teachings contained herein.

Figure 21:
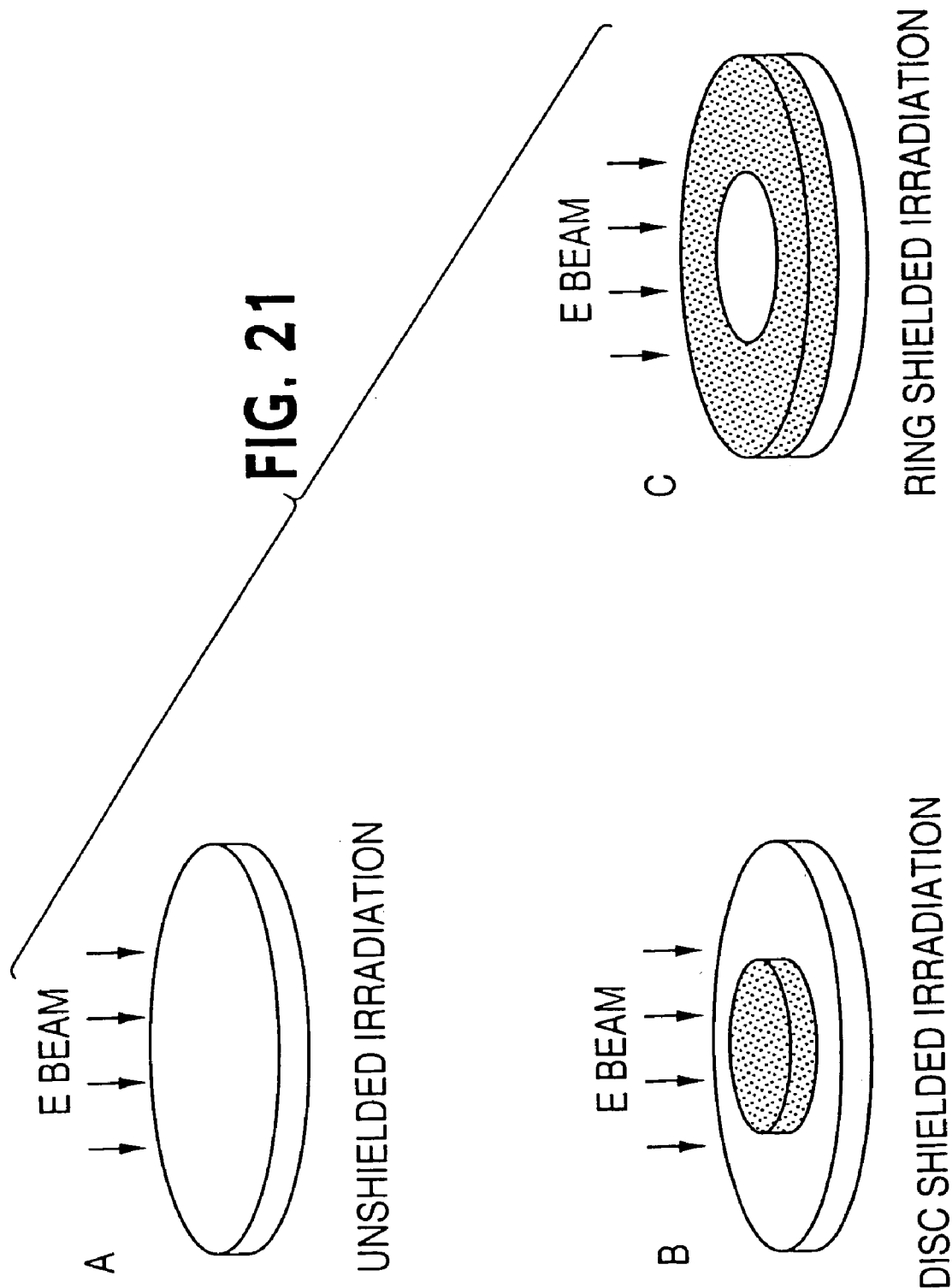
FIG. 21 illustrates the irradiation of a polymer preform using both a ring-shaped and disc-shaped shield in sequence.

Illustrative examples of suitable shield geometry's, cross-sections, and the use of shielding in sequence are shown in FIGS. 12–17 and 21. FIG. 21, for example, illustrates the irradiation of a polymer preform using both a ring-shaped and disc-shaped shield in sequence. Using a combination of ring and discs shields is an exemplary method of using shielding to impart different properties to the core and periphery of a polymer preform.

e. Complete Coverage vs. Partial Coverage Shielding

Figure 23:
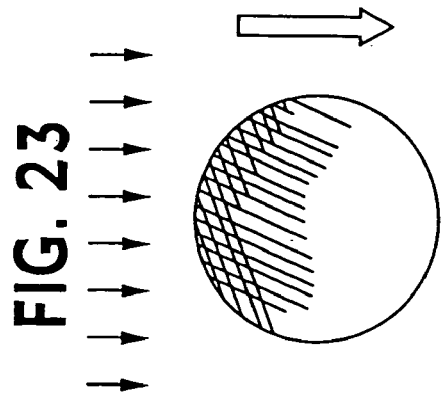
FIG. 23 illustrates an embodiment of complete coverage shielding as described herein.
Figure 24:
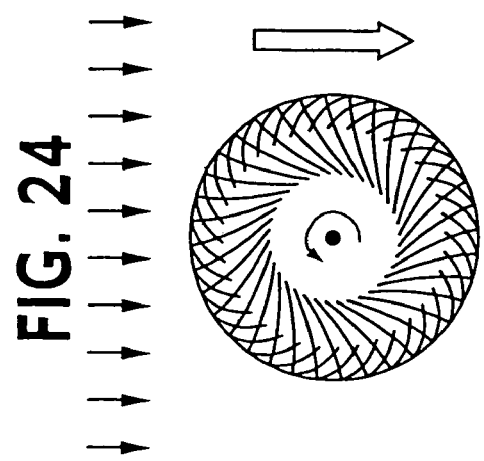
FIG. 24 illustrates another embodiment of complete coverage shielding as described herein.

"Complete" coverage shielding, denoting the use of a shield that covers the entire surface of the polymer being irradiated, is characterized by a cross-linking gradient parallel to the direction of irradiation. That is, due to the shield (including, for example, a portion of the polymer itself), there will be differences in the degree of cross-linking, resulting in a gradient ranging from extensively cross-linked to non-cross-linked, in the plane of the preform that is parallel to the vector that defines the direction of the radiation from the source to the preform. Examples of complete coverage shielding are shown in FIGS. 19, 23 and 24. In FIG. 23, the surface of the polymer is designed to be of sufficient thickness to act as a shield for the irradiation from the inner portion of the polymer. In other embodiments, other shields may be placed on or over the surface of the polymer such that the depth of penetration of irradiation, as the resulting cross-linking, is affected. FIG. 24 shows a particular embodiment of complete coverage shielding in which the preform is rotated along an axis passing through the interior of the preform. As FIG. 24 shows, this embodiment results in a gradient of cross-linking parallel to the vector that defines the direction of the radiation from the source to the preform and in which outer portion of the preform are more extensively cross-linked relative to the inner portion.

Figure 22:
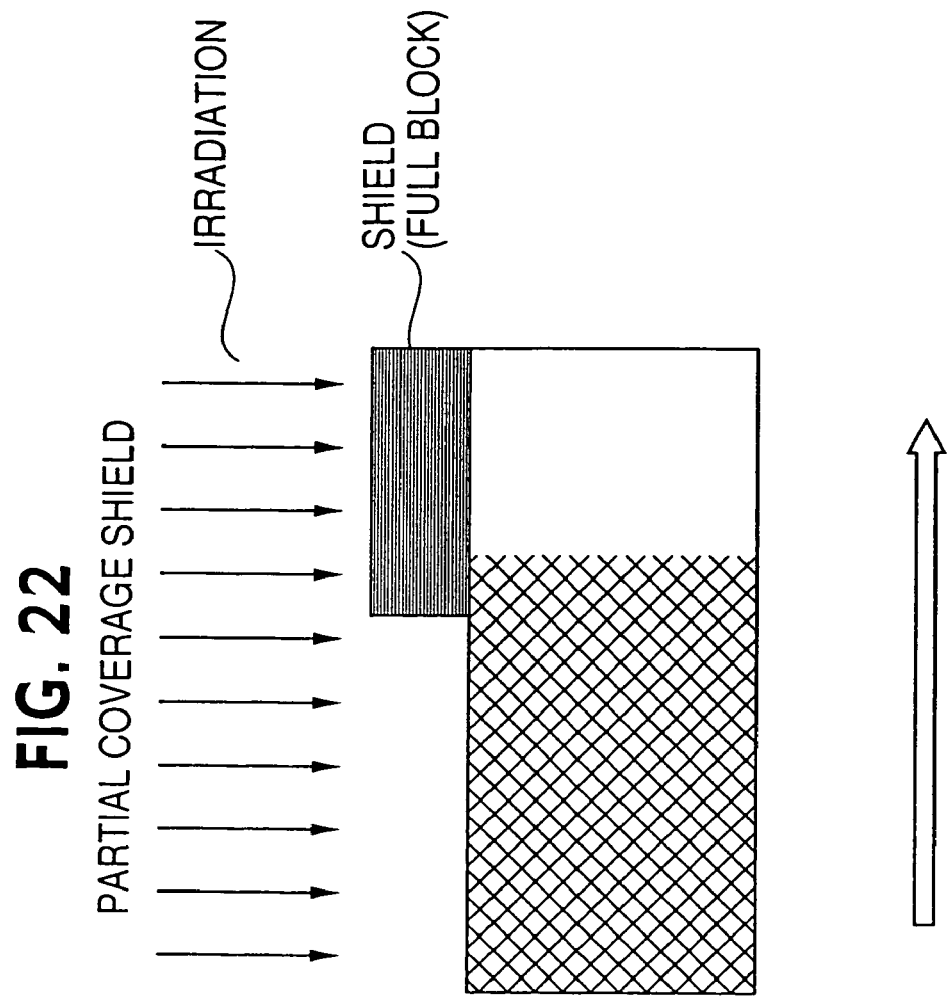
FIG. 22 illustrates an embodiment of partial coverage shielding as described herein.

"Partial" coverage shielding, denoting the use of a shield that does not cover the entire surface of the polymer being irradiated, is characterized by a cross-linking gradient perpendicular to direction of irradiation. That is, due to the shield, there will be differences in the degree of cross-linking, ranging from extensively cross-linked to non-cross-linked, in the plane of the preform that is perpendicular to the vector that defines the direction of the radiation from the source to the preform. FIG. 22. Due to propagation of the electrons in the irradiated preform, a degree of cross-linking will occur under the outer edges of the shield, which are schematically depicted as tear drops in FIG. 20. Thus, where differential shielding has been performed, a gradient of fuller cross-linking to comparatively lesser cross-linking or no crosslinking will be observed in the plane represented by the directional arrow in (see FIG. 22). Thus, cross-linking will be greatest in the unshielded areas, begin to decrease at the interface of the shield and an unshielded (or lesser shielded) edge, and decrease further, or be absent altogether (depending upon the thickness and consistency of the shield), at the inner portions under the shielded area.

4. Characterization Methodologies for Irradiated Polymers a. Thermal Properties (Differential Scanning Calorimetry—DSC)

The thermal properties of the polymers are studied using a Perkin Ehner DSC-7 at a heating and cooling rate of 10° C./min to determine the parameters needed in the thermodynamic analysis of the WIAM process for each polymer or polymer alloy. The heats of fusion, specific heats, crystallization, peak melting temperatures and crystallization temperatures are determined from the first heating and cooling endotherms. The cooling profile will be monitored to determine the variations in the crystallization behavior of the test samples.

b. Other Methodologies

Cross-link densities, infra-red analyses and other analytical techniques also can be performed on irradiated samples using approaches known in the art.

The invention is described in more detail in the following illustrative examples. Although the examples may represent only selected embodiments of the invention, it should be understood that the following examples are illustrative and not limiting.

5. Exemplary Uses for Orthopedic Applications and Other Examples a. Acetabular Liner This example describes a preferred embodiment of the selective, controlled manipulation of properties of polymers through radiation chemistry for the fabrication of an acetabular liner. In this embodiment, the acetabular liner is crosslinked where the articulation takes place. In the region of the locking mechanisms, the described acetabular liner is not crosslinked in order to maintain the properties of the raw polymer. The irradiation procedure is schematically described in FIG. 13. A preform polymer disc is shielded in the periphery during the irradiation process in order to avoid any crosslinking in the region where the locking mechanism of the liner is machined. As shown in this figure, the shield is placed around the periphery. Crosslinking then only takes place in the central region where the articulating surface of the acetabular liner will reside when the final shape is machined from the preform. The shield is circular and the dimensions of it is determined based on the size of the acetabular liner that will be machined. As shown in the figure, the shield is either a flat circular disc or a circular disc with an incline to generate a smooth transition of properties from crosslinked to uncrosslinked region. Subsequent to irradiation and prior to machining, the disc is heat treated to reduce the concentration of the residual free radicals to substantially undetectable levels as measured by electron spin resonance. The final component is machined carefully from the irradiated and annealed preform in order to make sure that the locking mechanisms are machined in the shielded region where there is no or little crosslinking and also the articulating surface is machined from the region where there is crosslinking achieved through the irradiation step of this example.

b. Mobile Bearing Knee I

Figure 14:
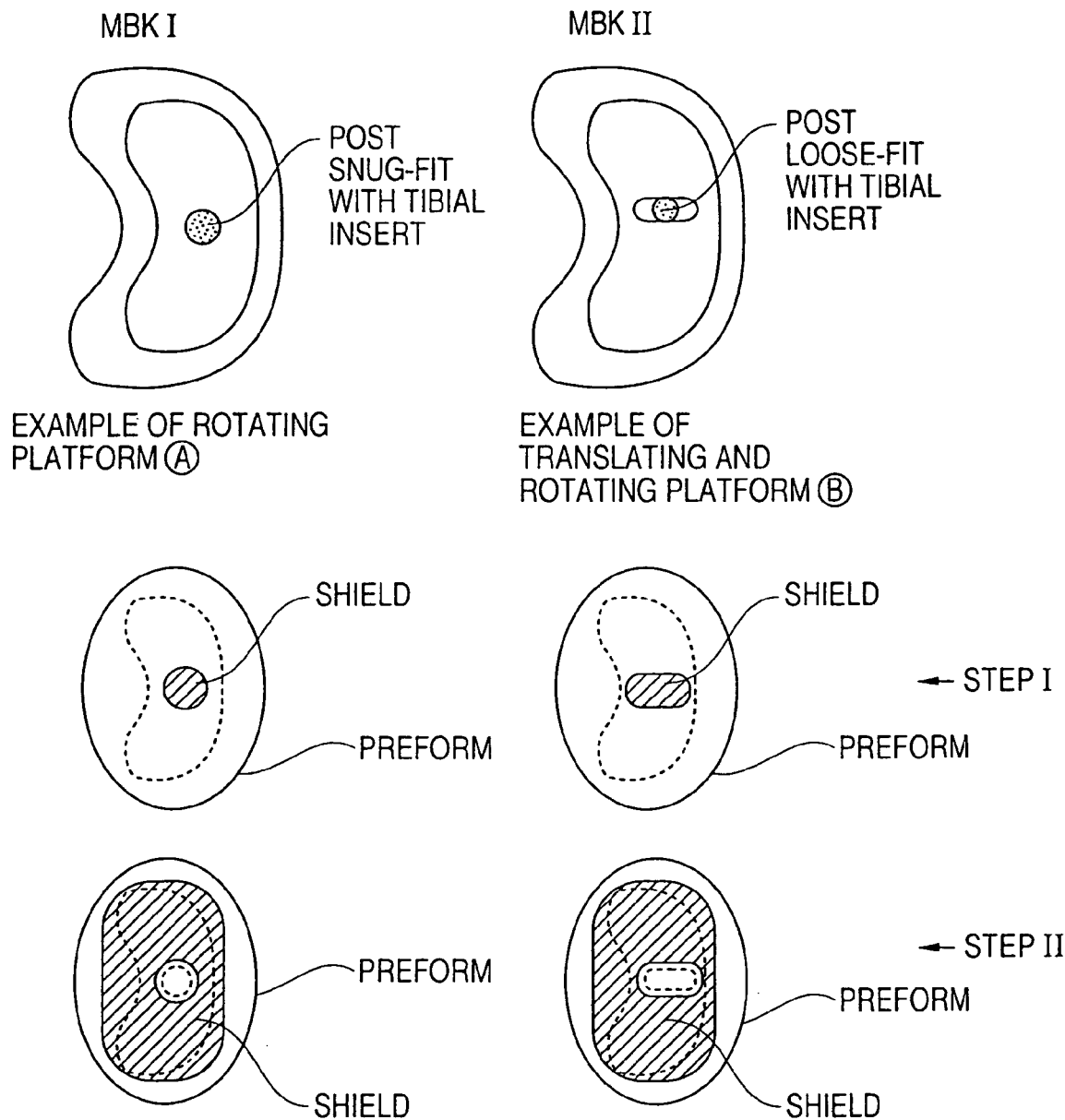
FIG. 14 depicts the use of the present invention in the fabrication of a mobile bearing knee prosthesis (such as a rotating platform knee).

In a mobile bearing knee (mbk), the tibial insert is free to move on the tibial base plate in different directions depending on the design. Because of this motion, the tibial insert will be in contact with stops that are machined onto the tibial plate. In order to minimize any long term cyclic deformation of the polymer insert in regions where contact with the stops occur, only the regions where the articulation will take place will be cross-linked. The contact regions will remain substantially uncross-linked. An example is schematically shown in FIG. 14. The shield(s) is placed on top of the preform from which the tibial insert will be machined. The location of the shield(s) is determined based on where the tibial insert will be engaging with the tibial base plate during motion. The dimensions of the shield are based on the design and the size of the tibial insert that will be machined from the preform. The shielded preform is irradiated with a preferred irradiation technique, the shield(s) is removed, and the preform is annealed above its melting point to reduce the concentration of the residual free radicals to substantially undetectable levels as measured by electron spin resonance. Finally, the preform is machined into the tibial insert while ensuring that uncrosslinked parts are maintained within regions where contact with stops will take place.

It is also possible to selectively manipulate the properties of the polymer used in the manufacturing of the mobile bearing tibial insert in regions where the insert will be in contact with the stops on the tibial base plate by the use of shielded radiation chemistry. This is achieved by adding a second irradiation step following the first one described in the above example. In this step, the preform is now shielded in regions where articulation will occur and only the regions where the tibial insert will eventually be in contact with the stops are subjected to irradiation. The preferred method of irradiation will then be used to irradiate the shielded preform construct in order to achieve the desired properties in the regions where the insert will be in contact with the stops. The desired properties could be a reduction in elastic modulus, which can be achieved through irradiation in the molten state.

c. Mobile Bearing Knee II

In another embodiment, also shown in FIG. 14, it is also possible to selectively manipulate the properties of the polymer use in the manufacturing of the mobile bearing tibial insert in regions where the insert will be rotating about a post on the tibial plate. This is achieved by shielded radiation chemistry. Similar to the embodiment described above, the polymer preform is irradiated with a shield placed on the preform to block the electrons from where the tibial insert will be rotating about the post. This ensures the crosslinking of the articulating surfaces and does not compromise the properties of the insert in the rotating region. Following the radiation, the shield is removed and the preform is annealed above its melting point to reduce the concentration of residual free radicals to substantially undetectable levels with electron spin resonance. In another embodiment, the properties of the region where the rotation of the tibial insert will occur can also be selectively controlled using shielded radiation chemistry. This is achieved by adding a second radiation step following the first one described in the above embodiment. The second step involves the irradiation of the preform with a shield covering only the articulating regions and not the region where the rotation will take place. The construct is then irradiated using the preferred radiation method, the shield is removed, the preform is annealed above its melting point to reduce the concentration of residual free radicals to substantially undetectable levels, and the component is machined. During the machining process, special care is taken to ensure that the rotating region of the tibial knee insert is machined from underneath the first shield.

d. Knee Meniscus

An artificial knee meniscus can be manufactured into the tibial insert used in total knee replacements. This is achieved by the shielded irradiation of a preform that will be used in the machining of the final tibial insert. The artificial meniscus is located around the periphery of the final component. The artificial meniscus should desirably have lower elastic modulus than the rest of the component. As shown in FIG. 15, a shield is placed on top of the preform in order to avoid any irradiation in the central region of the tibial plateau. This construct is then irradiated using the preferred electron beam irradiation method to achieve the desired level of elastic modulus. The first shield is then removed and replaced by another shield that covers the previously irradiated region. The shielded preform construct is then irradiated to crosslink the central region using the desired irradiation method to achieve the desired level of wear resistance.

e. Shoulder Meniscus

In total shoulder replacements, the major problem is the fixation of the glenoid the failure of which is initiated by the rocking motion induced by the humoral head. In order to reduce the rocking induced stresses at the glenoid-cement or glenoid-bone interface, a shoulder glenoid with a lower elastic modulus meniscus surrounding the periphery of the glenoid is manufactured. This is achieved similarly to the method described in the knee meniscus example. As depicted in FIG. 16, a shield is placed in the central region of the preform from which the glenoid will be machined. The shielded preform construct is then irradiated with the preferred method of irradiation that will lead to the desired level of reduction of the elastic modulus. This is followed by the shielding of the periphery and irradiation of the central region using a desired irradiation technique. The resulting product is then annealed in order to reduce the concentration of the residual free radicals to substantially undetectable levels as measured by electron spin resonance. Then the glenoid component is machined from the preform while ensuring that the regions selectively irradiated to achieve lower elastic modulus coincide with the synthetic meniscus or the periphery of the glenoid. In another embodiment, the reduced elastic modulus is limited to the superior and inferior regions of the glenoid where the rocking motion is most prominent. This is again achieved by the selective controlled manipulation of the properties through shielded irradiation methods.

f. Finger

Figure 17:
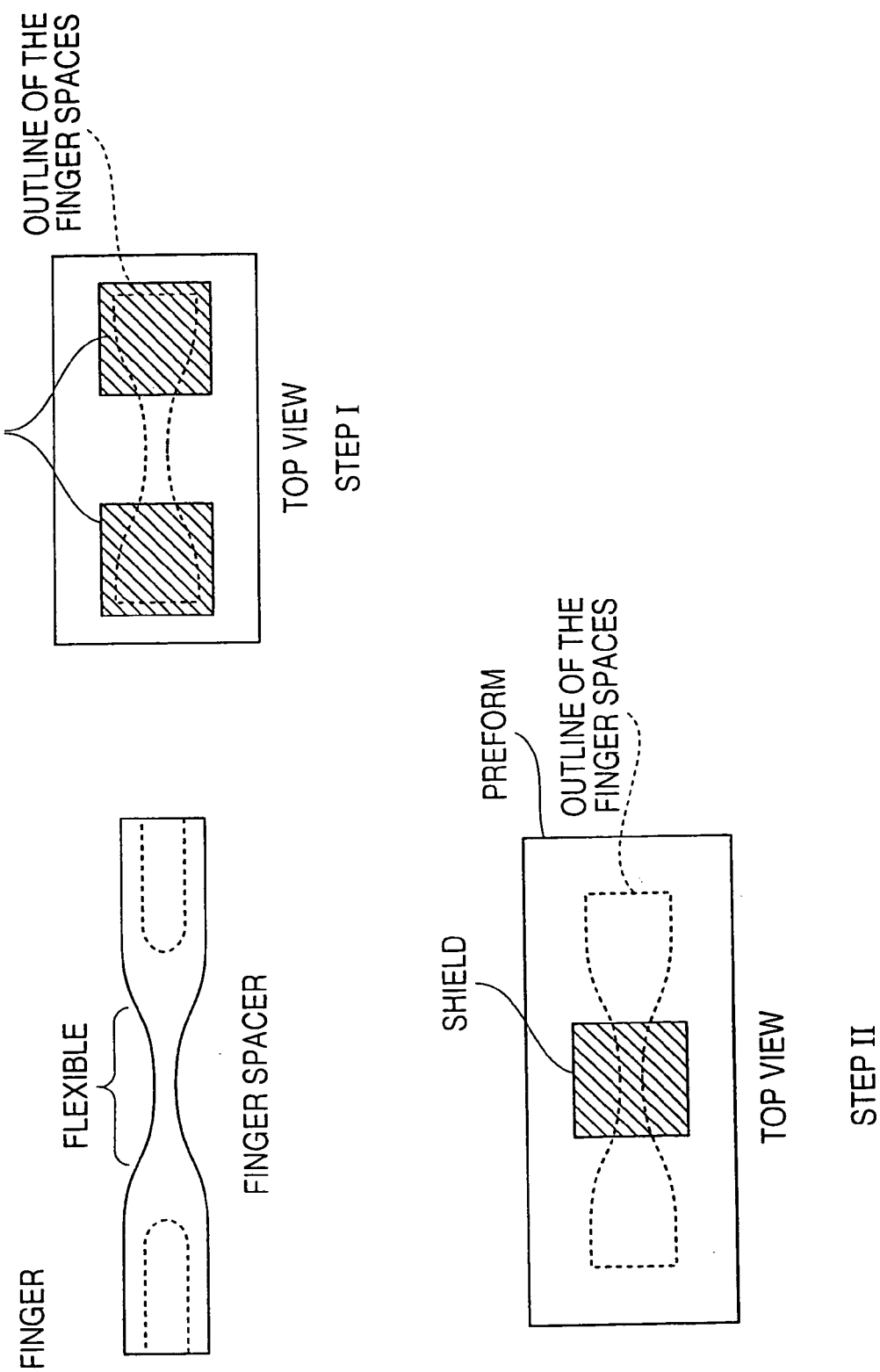
FIG. 17 depicts the use of the present invention in the fabrication of a spacer for a finger joint.

A spacer for a finger joint is designed to avoid bone-on-bone contact and bone-on-bone articulation. In order to accomplish this, a spacer using selective controlled manipulation of properties through radiation chemistry is manufactured. The proposed spacer is more compliant in regions where bending will occur to allow the motion of the finger. In the remaining regions, the spacer is less compliant and preferably wear resistant to prevent the generation of wear debris upon rubbing against bone or any surface that may be present. FIG. 17 schematically shows the irradiation process. The preform from which the final spacer device will be machined is irradiated with a shield in order to irradiate only the central region where the spacer will be bending during use. The irradiation method is selected to achieve a reduced elastic modulus (increased compliance), decreased stresses, and increased fatigue life of the material in that region. The first shielded irradiation is then followed by another irradiation step in which the central region is shielded and only the two extremes of the spacer areas are irradiated using the desired irradiation method. Following the two steps of shielded irradiation, the preform is annealed in order to reduced the concentration of the residual free radicals to substantially undetectable levels as measured by electron spin resonance. The machining of the spacer is then carried out carefully to ensure that the region where the elastic modulus is lower is maintained at the central region where the bending of the spacer will take place during use.

g. High Flex Knee

One of the major limitations of total knee replacements is the reduced range of motion of the knee following the operation. An increased range of motion, that is increased flexion of the knee, is desirable especially for cultures where deep knee bends are part of daily activities. For instance, in Islamic cultures, high flexion of the knee is required for praying. In a total knee replacement in order to achieve deeper flexion angles, the femoral component would have to further translate posteriorly. This, in most designs, will lead to the edge loading of the posterior condyles of the tibial insert with the femoral component. The result of this type of loading will be very high contact stresses and the potential premature failure of the edge of the tibial condyles. The likelihood of snap mechanism failure and location of the tibial insert from the metal base plate will also increase. To avoid these types of failures, improved total knee designs with increased flexion angle will be needed.

To further reduce the risk of failure in either the existing or new designs, one can selectively manipulate the properties of the polyethylene at the posterior edges of the condyles to reduce the contact stresses. This can be done through selective controlled manipulation of the properties of the polyethylene used in the manufacture of the tibial insert. For instance, the tibial knee insert can be made up of warm irradiated, adiabatically melted (WIAM at 95 kGy of radiation dose and 125° C. of pre-irradiation temperature) UHMWPE with the posterior condyles treated further with melt irradiation (IMS at 100 kGy at irradiation temperature of 140° C.). The further treatment with the IMS process will reduce the modulus of the already WIAM-treated polymer, hence reducing the contact stresses. This will also lead to reduced load transfer to the snap and locking mechanisms, hence preventing snap/locking mechanism failures.

A similar result could be achieved by machining the tibial knee insert from a piece of UHMWPE that had been partially treated with a 125° C., 95 kGy WIAM process and partially treated with a 140° C., 100 kGy IMS process. The tibial knee insert is machined so that the posterior edges of the condyles coincide with the part of the UHMWPE where IMS had been applied and the rest coincides with where the WIAM treatment had been applied.

6. Irradiation Parameters and Controlled Manipulation of Irradiated Polymer Properties a. Iso-Dose Penetration The irradiation of materials with electrons leads to the well known built-up of absorbed dose level as a function of distance away from the electron beam incidence surface. This built-up of the absorbed dose is due to the generation of secondary electrons following the collision of the incident electrons with the atoms of the host material. The collisions generate more electrons at the expense of loosing kinetic energy while increasing the effective absorbed dose level as the electron flux travels into the material. At a critical depth, the kinetic energy loss reaches a level where the electron flux slows down and leads to an abrupt decay in the absorbed dose level. The depth at which the absorbed dose level is equal to that at the surface is called the iso-dose penetration depth. This penetration increases with the increasing energy of the incident electrons. Provided herein are two methods of determining the iso-dose penetration of 10 MeV electrons into UHMWPE, namely dosimetry and determination of trans-vinlyene unsaturations.

Figure 25:
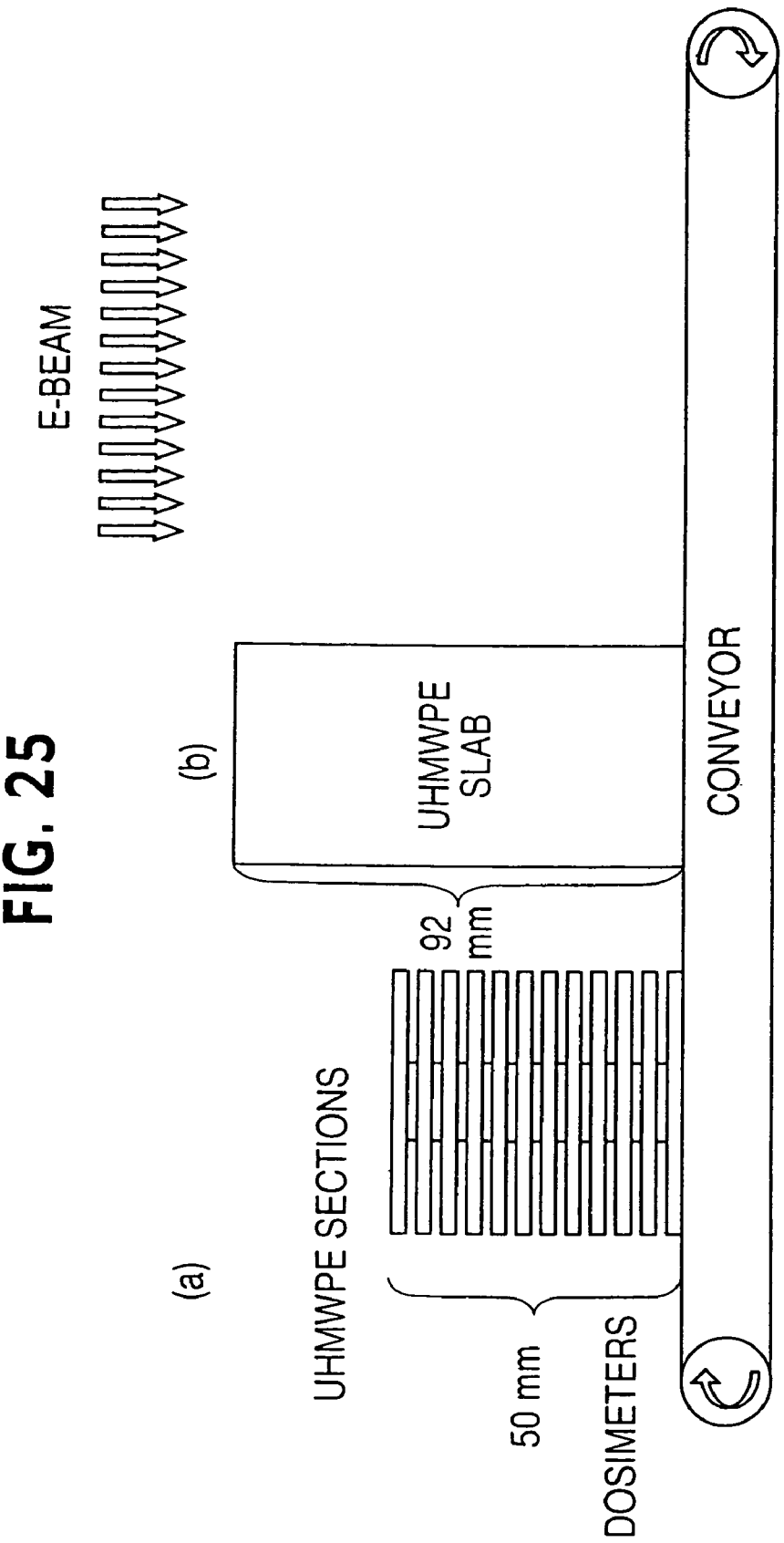
FIG. 25 illustrates (a) the irradiation of the thin sections sandwiched with dosimeters along with (b) the 96 mm thick sample. The former was used in determining the e-beam cascade using the TVI method, while the latter was used to determine the cascade by evaluating the absorbed dose levels in the sandwiched dosimeters.

For the dosimetry, irradiation was performed on a stack of 16 thin sections (3 mm) of UHMWPE (GUR 1050) sandwiched with three Far West Technology (Goleta, Calif.) dosimeters between each section as shown in FIG. 25. The dosimeters were then used to calculate an average dose level as a function of e-beam penetration depth. Additionally, a 96 mm thick disc was irradiated, which was used for the trans-vinylene method of quantifying the beam penetration. The e-beam irradiation was carried out using a 10 MeV accelerator, Impela 10/50 (E-Beam Services, NJ, USA) operated at 40 kW power.

The 96 mm thick disc was microtomed (200 µm section) in the direction of the e-beam penetration. IR-spectra from this thin section were collected using a BioRad UMA 500 infra-red microscope. The spectra were collected as a function of distance away from the e-beam incidence surface with a step size of 1 mm. IR spectra were collected on lightly polished microtomed sections using a BioRad UMA500 IR-microscope with an aperture size of 100 µm by 50 µm as a function of depth away from the e-beam incidence surface at 1 mm increments. The trans-vinylene index (TVI) was calculated by normalizing the area under the trans-vinylene vibration at 965 cm$^{-1}$ to that under the 1900 cm$^{-1}$ vibration after subtracting the respective baselines. The following equation was used:

$$TVI = \frac{\int_{950}^{980} A(w)\,dw - B_1}{\int_{1850}^{1985} A(w)\,dw - B_2}$$

$$B_1 = \frac{[A(980) + A(950)](980 - 950)}{2}$$

$$B_2 = \frac{[A(1850) + A(1985)](1985 - 1880)}{2}$$

where A(w) is the infra-red absorbance measured at wave number, w, $B_1$ is the area under the baseline of the trans-vinylene vibration and $B_2$ is that of the baseline under the reference (1900 cm$^{-1}$) vibration.

Figure 26:
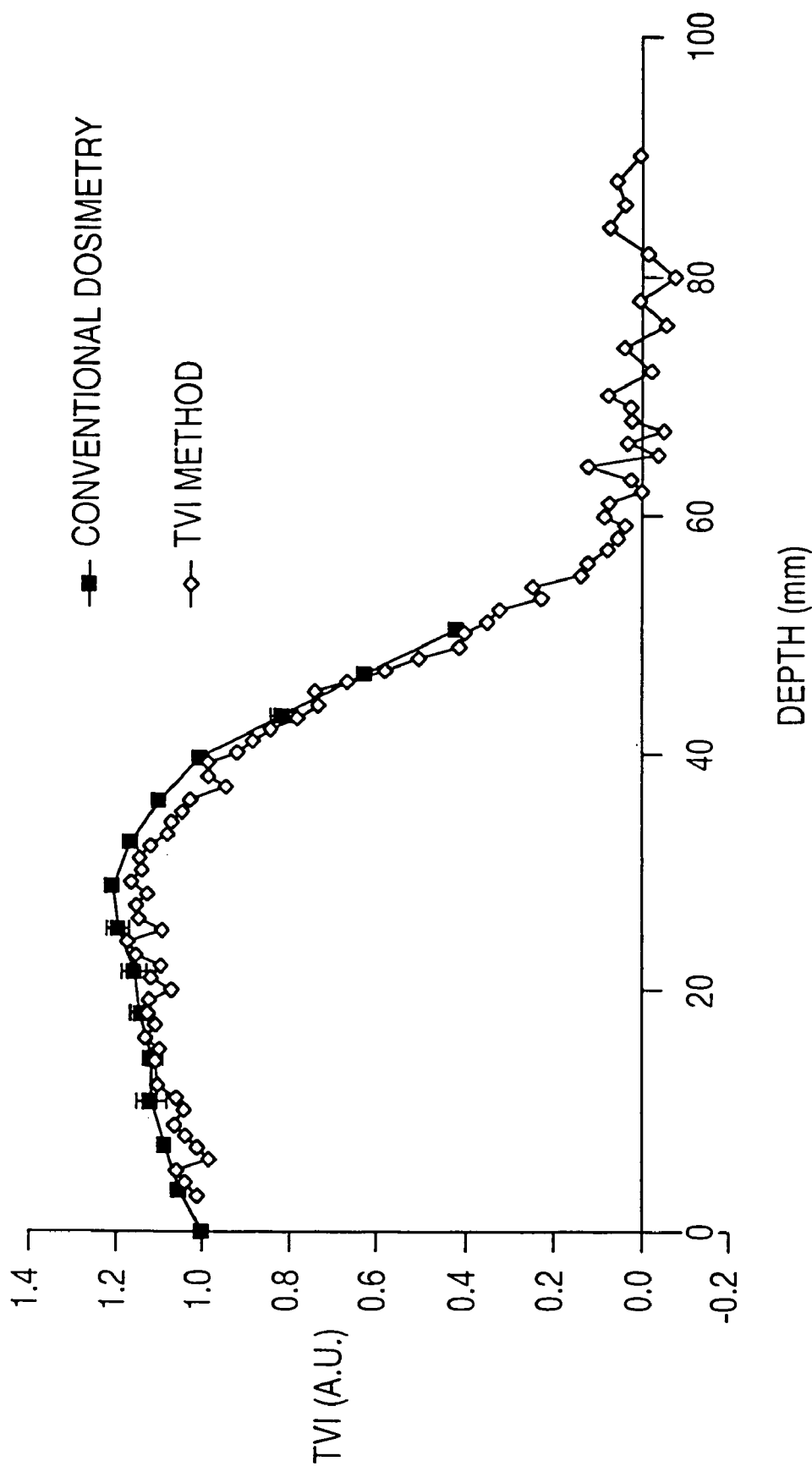
FIG. 26 shows the normalized TVI variation as a function of depth away from e-beam incidence surface as compared with the normalized dose level measured through the Far West dosimeters. The agreement between the two curves supports that the TVI yield is directly proportional to the absorbed dose level

FIG. 26 shows the dosimeter measurement of the cascade effect and that of the TVI method, where both the TVI values and the values obtained from the dosimetry were normalized to their respective values measured at the e-beam incidence surface. Both sets of data were in good agreement, which shows strong evidence for the validity of the TVI method in determining the dose variation as a result of the cascade effect. The build-up of the absorbed dose level is apparent with both methods and the approximate iso-dose penetration of the 10 MeV e-beam used is about 40 mm into UHMWPE.

b. Selective Controlled Reduction of the Elastic Modulus

The elastic modulus of the polymer can be reduced by using several different techniques. In one embodiment, the polymer is irradiated in its molten state in order to reduce the crystallinity and elastic modulus of the polymer. In another embodiment, the polymer is irradiated using the WIAM technique and the elastic modulus is reduced by increasing the irradiation dose levels. In another embodiment, the polymer is irradiated using the CISM technique and the elastic modulus is reduced by using increased radiation dose levels. In a medical device such as a finger joint spacer, shoulder meniscus, knee meniscus, or tibial knee inserts the regions where the elastic modulus is desirably lower can be achieved by using any one of the above techniques. In one embodiment, the preform from which the device will be machined is shielded so that the electron beam penetration is limited to those regions that will selectively be treated to have lower elastic modulus. The preform is then irradiated with the desired irradiation method, such as WIAM, irradiation in a molten state, or CISM. The shield is then removed and the preform is further irradiated with the desired method without any more shielding. This leads to much higher cumulative dose levels in initially irradiated regions, where the low elastic modulus is desired. The higher dose levels in these regions will then lead to lower elastic modulus compared with the rest of the preform. In another embodiment, the preform from which the medical device will be machined is irradiated with two steps of shielded irradiation. First, the regions with the desired high elastic modulus are shielded against radiation and the irradiation is carried out in order to reduce the elastic modulus of the regions that were exposed to the electron beam. The methods of irradiation could be selected from any one of the methods described above. Then the shield is removed and replaced by another shield whereby the regions with the now lower elastic modulus are covered to prevent or minimize further exposure. This shielded preform construct is then irradiated with the preferred irradiation method to achieve the desired properties outside the regions with lower elastic modulus. Following the second irradiation step, the shield is removed and the preform is annealed in order to reduce the concentration of the residual free radicals to undetectable levels as measured by electron spin resonance. Finally, the medical device is machined from the preform with care to make sure that the lower elastic modulus regions coincide with parts of the medical device that are intended to have lower elastic modulus, for instance, the meniscus in the tibial knee insert or the bending portion of the finger joint.

c. Residual Free Radicals

Depending on the polymer system used in the selective controlled manipulation of properties in a preform to manufacture any of the medical devices described in the above embodiments, there may or may not be detectable residual free radicals left in the material following the irradiation process. If there are residual free radicals remaining in the material, these are reduced to substantially undetectable levels as measured by electron spin resonance through annealing of the preforms above the melting point of the polymeric system used. The melt annealing allows the residual free radicals to re-combine with each other. If for a given system the preform substantially does not have any detectable residual free radicals following irradiation, then the melt annealing step is not utilized and the irradiated preform is directly machined into the final medical device.

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications and patent applications cited herein, including U.S. Pat. No. 5,879,400, U.S. Provisional Application Ser. No. 60/254,560, International Application No. PCT/US97/02220 (WO 97/29793), and International Application No. PCT/US99/16070, are expressly incorporated herein by reference in their entireties to the same extent as if each were incorporated by reference individually.

I claim:

1. An irradiated polymeric composition comprising polymers, wherein the polymeric composition has a gradient of crosslink density in a direction perpendicular to the direction of irradiation, wherein a part of the polymeric composition was preferentially shielded to partially block radiation during irradiation in order to provide the gradient of crosslink density, wherein the preferential shielding is used where a gradient of crosslink density is desired and the gradient of crosslink density is in a direction perpendicular to the direction of irradiation on the preferentially shielded polymeric composition.

2. The composition of claim 1, wherein said polymer is selected from the group consisting of high density polyethylene, low density polyethylene, linear low density polyethylene, ultra low density polyethylene, very low density polyethylene, ultra high molecular weight polyethylene, and high molecular weight polyethylene.

3. The composition comprising of claim 1, wherein the polymer is an alloy of two or more polymers selected from the group consisting of high density polyethylene, low density polyethylene, linear low density polyethylene, ultra low density polyethylene, very low density polyethylene, ultra high molecular weight polyethylene, and high molecular weight polyethylene.

4. The composition of claim 1, wherein the polymer is ultra high molecular weight polyethylene.

5. A method of making a cross-linked polymeric composition comprising polymers, wherein the cross-linked polymeric composition has a gradient of crosslink density in a direction perpendicular to the direction of irradiation, said method comprising:

(A) preferentially shielding to partially block radiation from a part of the composition; and (B) irradiating said preferentially shielded composition of (A) in order to provide the gradient of crosslink density, wherein the preferential shielding is used where a gradient of crosslink density is desired and the gradient of crosslink density is in a direction perpendicular to the direction of irradiation of the preferentially shielded polymeric composition.

6. The method of claim 5, wherein said polymer is selected from the group consisting of high density polyethylene, low density polyethylene, linear low density polyethylene, ultra low density polyethylene, very low density polyethylene, ultra high molecular weight polyethylene, and high molecular weight polyethylene.

7. The method of claim 6, wherein the polymer is ultra high molecular weight polyethylene.

8. The method of claim 5, wherein irradiation step comprises one or more, in any order, of the procedures selected from the group consisting of procedures (a)–(g):

(a) (i) heating the polymer to at or above the melting temperature of the polymer, and
(ii) irradiating the polymer in the molten state;

(b) (i) providing the polymer at or below room temperature, and
(ii) irradiating the polymer;

(c) (i) providing the polymer at or below room temperature, and
(ii) irradiating the polymer with a high enough total dose and/or at a fast enough dose rate to generate enough heat in the polymer to result in at least a partial melting bf the crystals of the polymer;
(d) (i) providing the polymer at or below room temperature,
(ii) irradiating the polymer, and
(iii) heating the irradiated polymer to at or above the melting temperature of the polymer;
(e) (i) heating the polymer to a temperature above room temperature and below the melting temperature, and
(ii) irradiating the heated polymer;
(f) (i) heating the polymer to a temperature above room temperature and below the melting temperature,
(ii) irradiating the heated polymer, and
(iii) heating the irradiated polymer to at or above the melting temperature of the polymer; and
(g) (i) heating the polymer to a temperature above room temperature and below the melting temperature, and
(ii) irradiating the heated polymer with a high enough total dose and/or at a fast enough dose rate to generate enough heat in the polymer to result in at least a partial melting of the crystals of the polymer.

9. The method of claim 5, wherein said polymeric composition is shielded by a shield made from a material selected from the group consisting of ceramics, metals, glasses and polymers.

10. A medical prosthesis comprising an irradiated polymeric composition comprising polymers, wherein the prosthesis has a gradient of crosslink density in a direction perpendicular to the direction of irradiation, wherein a part of the polymeric composition was preferentially shielded to partially block radiation during irradiation in order to provide the gradient of crosslink density, wherein the preferential shielding is used where a gradient of crosslink density is desired and the gradient of crosslink density is in a direction perpendicular to the direction of irradiation on the preferentially shielded polymeric composition.

11. The medical prosthesis of claim 10, wherein said polymer is selected from the group consisting of high density polyethylene, low density polyethylene, linear low density polyethylene, ultra low density polyethylene, vey low density polyethylene, ultra high molecular weight polyethylene, and high molecular weight polyethylene.

12. The medical prosthesis of claim 10, wherein the polymer is an alloy of two or more polymers selected from the group consisting of high density polyethylene, low density polyethylene, linear low density polyethylene, ultra low density polyethylene, very low density polyethylene, ultra high molecular weight polyethylene, and high molecular weight polyethylene.

13. The medical prosthesis of claim 10, wherein the polymer is ultra high molecular weight polyethylene.

14. A method of making a medical prosthesis comprising an irradiated polymeric composition, wherein the medical prosthesis has a gradient of crosslink density in a direction perpendicular to the direction of irradiation, said method comprising:
(A) preferentially shielding to partially block radiation from a part of the composition; and
(B) irradiating said preferentially shielded composition of (A) in order to provide the gradient of crosslink density, wherein the preferential shielding is used where a gradient of crosslink density is desired and the gradient of crosslink density is in a direction perpendicular to the direction of irradiation on the preferentially shielded polymeric composition.

15. The method of claim 14, wherein said polymer is selected from the group consisting of high density polyethylene, low density polyethylene, linear low density polyethylene, ultra low density polyethylene, very low density polyethylene, ultra high molecular weight polyethylene, and high molecular weight polyethylene.

16. The method of claim 14, wherein the polymer is ultra high molecular weight polyethylene.

17. The method of claim 14, wherein irradiation step comprises one or more, in any order, of the procedures selected from the group consisting of procedures (a)–(g):
(a) (i) heating the polymer to at or above the melting temperature of the polymer, and
(ii) irradiating the polymer in the molten state;
(b) (i) providing the polymer at or below room temperature, and
(ii) irradiating the polymer;
(c) (i) providing the polymer at or below room temperature, and
(ii) irradiating the polymer with a high enough total dose and/or at a fast enough dose rate to generate enough heat in the polymer to result in at least a partial melting of the crystals of the polymer;
(d) (i) providing the polymer at or below room temperature, (ii) irradiating the polymer, and
(iii) heating the irradiated polymer to at or above the melting temperature of the polymer;
(e) (i) heating the polymer to a temperature above room temperature and below the melting temperature, and
(ii) irradiating the heated polymer;
(f) (i) heating the polymer to a temperature above room temperature and below the melting temperature,
(ii) irradiating the heated polymer, and
(iii) heating the irradiated polymer to at or above the melting temperature of the polymer; and
(g) (i) heating the polymer to a temperature above room temperature and below the melting temperature, and
(ii) irradiating the heated polymer with a high enough total dose and/or at a fast enough dose rate to generate enough heat in the polymer to result in at least a partial melting of the crystals of the polymer.

18. The method of claim 14, wherein said polymeric composition is shielded by a shield made from a material selected from the group consisting of ceramics, metals, glasses and polymers.

19. An irradiated polymeric composition comprising polymers, wherein the polymeric composition has a gradient of crosslink density in a direction perpendicular to the direction of irradiation, wherein the gradient of crosslink density is obtained by partial coverage shielding of the polymeric composition to partially block radiation, wherein partial coverage shielding is used where a gradient of crosslink density is desired and the gradient of crosslink density is in a direction perpendicular to the direction of irradiation on the partial coverage shielding.

20. A medical prosthesis comprising an irradiated polymeric composition comprising polymers, wherein the prosthesis has a gradient of crosslink density in a direction perpendicular to the direction of irradiation, wherein the gradient of crosslink density is obtained by partial coverage shielding of the polymeric composition to partially block radiation, wherein the partial coverage shielding is used where a gradient of crosslink density is desired and the gradient of crosslink density is in a direction perpendicular to the direction of irradiation on the partial coverage shielding.

21. A method of making a cross-linked polymeric composition comprising polymers, wherein the cross-linked polymeric composition has a gradient of crosslink density in a direction perpendicular to the direction of irradiation, wherein the method comprising:
(A) partial coverage shielding of the polymeric composition to partially block radiation; and
(B) Irradiating the partially shielded composition of (A) in order to provide the gradient of crosslink density, wherein the partial coverage shielding is used where a gradient of crosslink density is desired and the gradient of crosslink density is in a direction perpendicular to the direction of irradiation on the partial coverage shielding.

22. A method of making a medical prosthesis comprising an irradiated polymeric composition comprising polymers, wherein the medical prosthesis has a gradient of crosslink density in a direction perpendicular to the direction of irradiation, said method comprising:
(A) partial coverage shielding of the composition to partially block radiation; and
(B) irradiating the partially shielded composition of (A) in order to provide the gradient of crosslink density, wherein the partial coverage shielding is used where a gradient of crosslink density is desired and the gradient of crosslink density is in a direction perpendicular to the direction of irradiation on the partial coverage shielding.

* * * * *